(12) United States Patent
Sganga et al.

(10) Patent No.: US 12,370,345 B2
(45) Date of Patent: Jul. 29, 2025

(54) SYSTEMS, METHODS, AND DEVICES FOR ADVANCING AN ENDOVASCULAR INSTRUMENT

(71) Applicant: Remedy Robotics, Inc., San Francisco, CA (US)

(72) Inventors: Jake Anthony Sganga, San Francisco, CA (US); David James Bell, Mill Valley, CA (US); Hugo Louis Seize, San Francisco, CA (US)

(73) Assignee: REMEDY ROBOTICS, INC., San Francisco, CA (US)

( * ) Notice: Subject to any disclaimer, the term of this patent is extended or adjusted under 35 U.S.C. 154(b) by 0 days.

(21) Appl. No.: 18/968,770

(22) Filed: Dec. 4, 2024

(65) Prior Publication Data

US 2025/0090805 A1 Mar. 20, 2025

Related U.S. Application Data

(63) Continuation-in-part of application No. 18/676,954, filed on May 29, 2024.
(Continued)

(51) Int. Cl.
*A61M 25/01* (2006.01)
*A61B 34/30* (2016.01)
*A61M 25/09* (2006.01)

(52) U.S. Cl.
CPC ......... *A61M 25/0113* (2013.01); *A61B 34/30* (2016.02); *A61M 25/09* (2013.01); *A61B 2034/301* (2016.02)

(58) Field of Classification Search
CPC ... A61M 25/0113; A61M 25/09; A61B 34/30; A61B 2034/301
See application file for complete search history.

(56) References Cited

U.S. PATENT DOCUMENTS 8,740,840 B2 * 6/2014 Foley ............... A61M 25/0136
 604/95.01
9,005,217 B2 * 4/2015 Govari .................. A61B 34/30
 604/95.01
(Continued)

FOREIGN PATENT DOCUMENTS

WO WO 2018-186690 A1 10/2018

OTHER PUBLICATIONS

International Search Report for International Application No. PCT/US2024/031466 dated Sep. 23, 2024.
(Continued)

*Primary Examiner* — Sean P Dougherty
(74) *Attorney, Agent, or Firm* — Knobbe Martens Olson & Bear LLP

(57) ABSTRACT

A system for moving an elongate tool through a lumen can include a proximal device and a distal device. The proximal device moves linearly in proximal and distal directions and includes a proximal shutter that between an open state in which an elongate tool moves freely through the proximal shutter and a closed state in which the elongate tool is fixedly held by the proximal shutter. The distal device moves linearly in the proximal and distal directions and includes a distal shutter that transitions between an open state in which the elongate tool moves freely through the distal shutter and a closed state in which the elongate tool is fixedly held by the distal shutter. The motions of the proximal and distal devices can be coordinate to provide smooth, continuous, and/or uninterrupted insertion or retraction of the elongate tool.

24 Claims, 25 Drawing Sheets

Related U.S. Application Data

(60) Provisional application No. 63/504,943, filed on May 30, 2023.

(56) References Cited

U.S. PATENT DOCUMENTS

| | | | |
|---|---|---|---|
| 10,695,536 B2 * | 6/2020 | Weitzner | A61B 18/14 |
| 10,940,292 B2 * | 3/2021 | Bagwell | A61M 25/09041 |
| 11,278,703 B2 * | 3/2022 | Kokish | A61M 25/0113 |
| 12,035,989 B2 * | 7/2024 | Clark | A61B 34/25 |
| 12,239,405 B2 * | 3/2025 | Stepanauskas | A61B 34/30 |
| 2008/0009791 A1 | 1/2008 | Cohen et al. | |
| 2014/0276389 A1 | 9/2014 | Walker | |
| 2019/0240462 A1 | 8/2019 | Parodi et al. | |
| 2019/0351187 A1 | 11/2019 | Choi et al. | |
| 2020/0405413 A1 | 12/2020 | Kokish et al. | |
| 2022/0233264 A1 | 7/2022 | Klem et al. | |
| 2023/0070004 A1 | 3/2023 | Yu | |
| 2023/0128853 A1 | 4/2023 | Lindekugel et al. | |
| 2024/0399117 A1 | 12/2024 | Sganga et al. | |

OTHER PUBLICATIONS

International Search Report for International Application No. PCT/US2024/058504 dated Mar. 19, 2025.

* cited by examiner

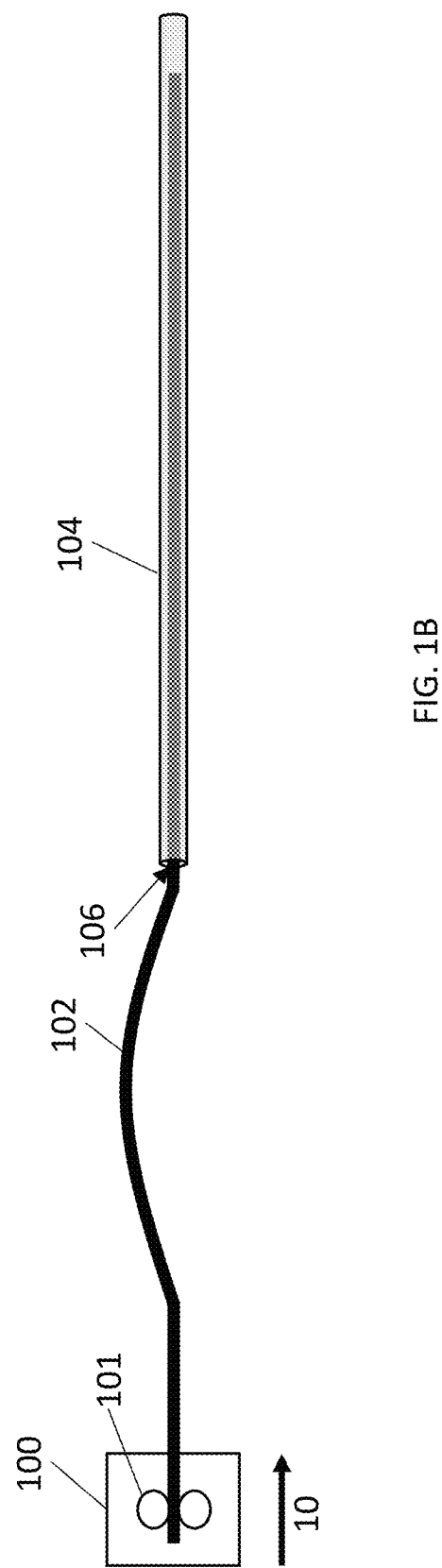

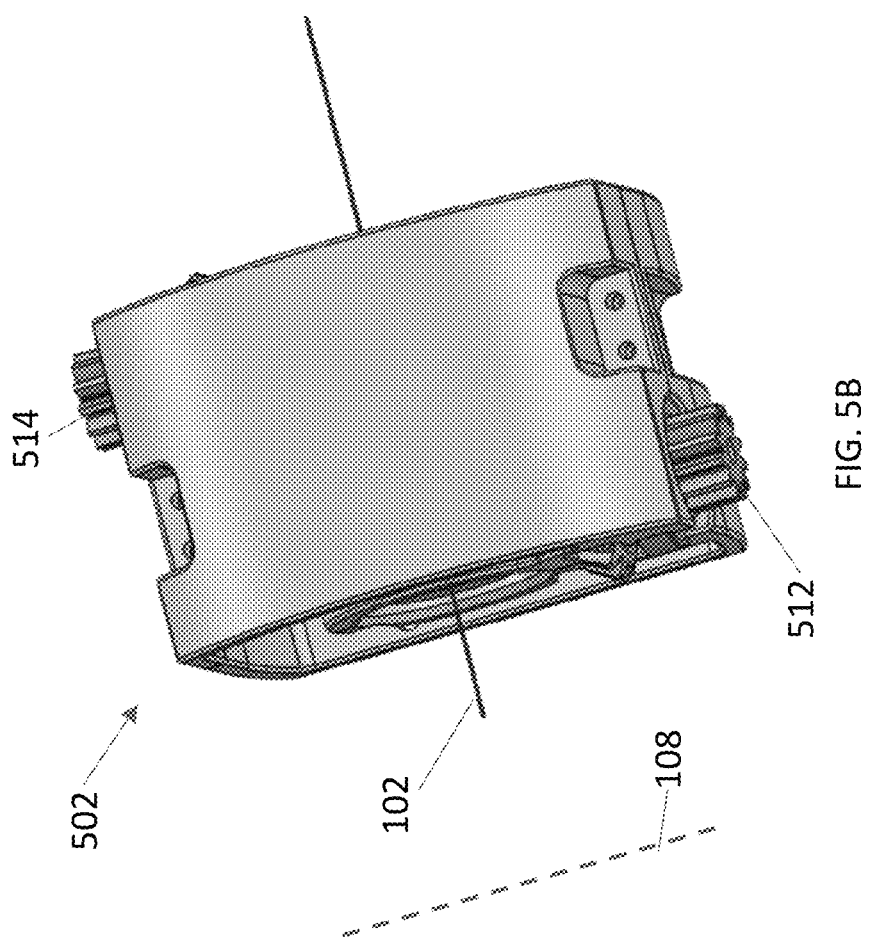

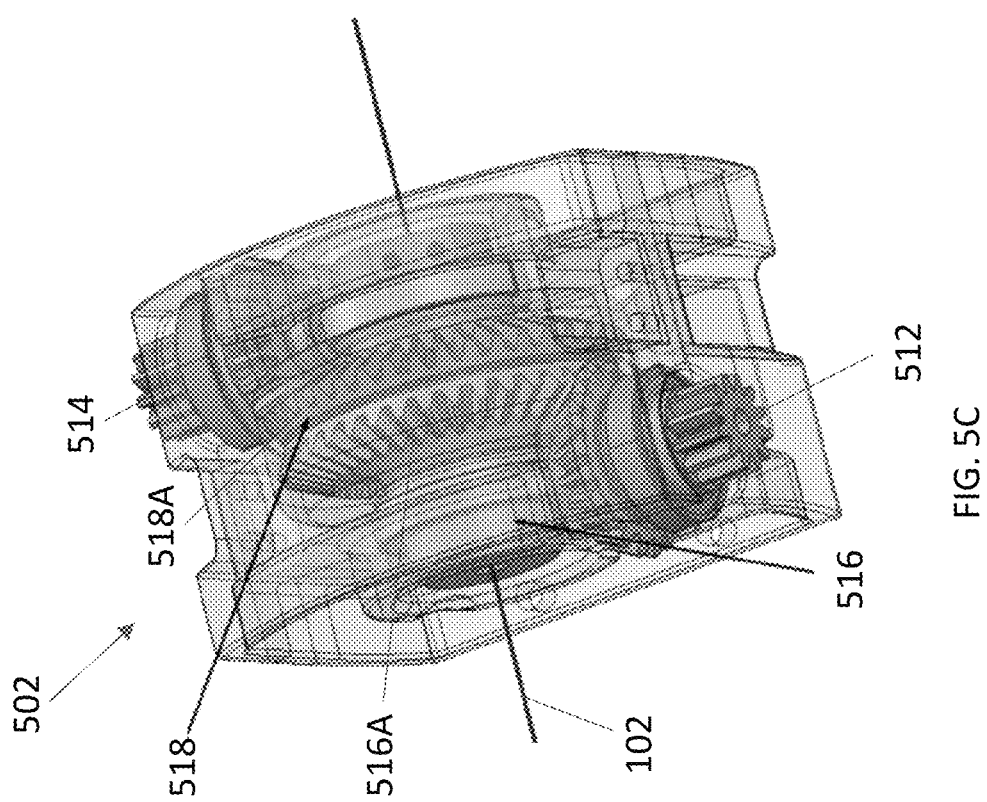

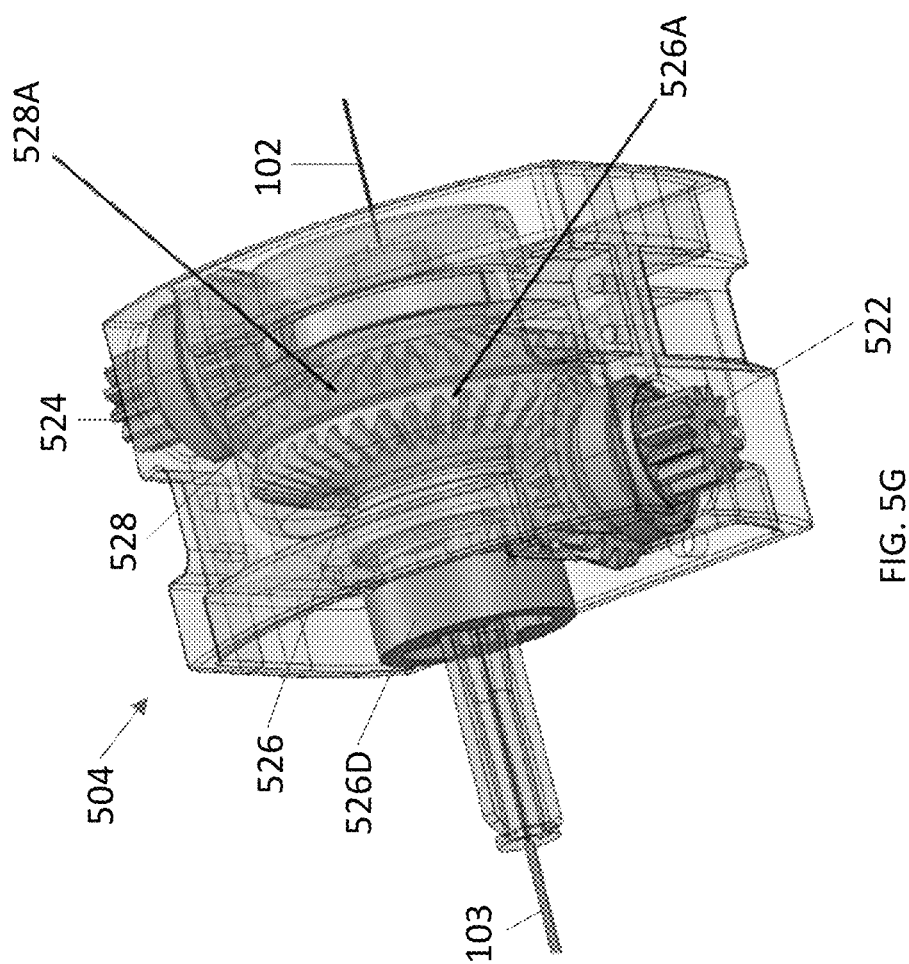

1) PROXIMAL is closed, DISTAL is closing

CONFIGURATIONS 6 > 5

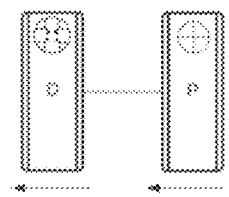

2) PROXIMAL is opening, DISTAL is closed

CONFIGURATIONS 5 > 4

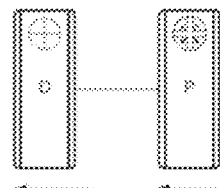

3) PROXIMAL is opened and resetting, DISTAL is closed

CONFIGURATIONS 4 > 3

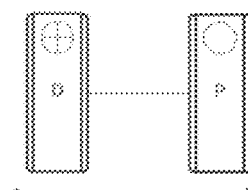

4) PROXIMAL is opened and reset, DISTAL is closed

CONFIGURATION 3

5) PROXIMAL is closing, DISTAL is closed

CONFIGURATIONS 3 > 2

6) PROXIMAL is closed, DISTAL is opening

CONFIGURATIONS 2 > 1

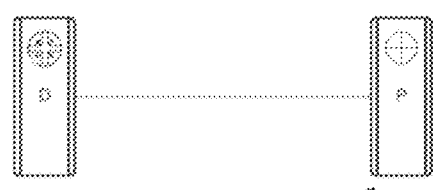

7) PROXIMAL is closed, DISTAL is opened and resetting

CONFIGURATIONS 1 > 8

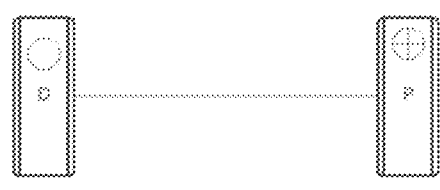

8) PROXIMAL is closed, DISTAL is opened and reset

CONFIGURATION 8

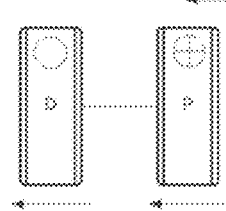

FIG. 8

1) PROXIMAL is closing, DISTAL is closed

CONFIGURATIONS 4 > 5

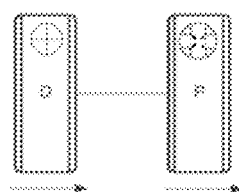

2) PROXIMAL is closed, DISTAL is opening

CONFIGURATIONS 5 > 6

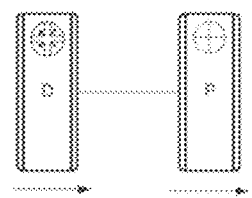

3) PROXIMAL is closed, DISTAL is opened and resetting

CONFIGURATIONS 6 > 1

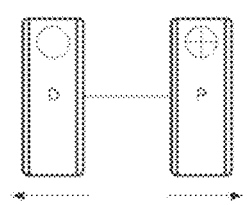

4) PROXIMAL is closed, DISTAL is opened and reset

CONFIGURATION 1

5) PROXIMAL is closed, DISTAL is closing

CONFIGURATIONS 1 > 2

6) PROXIMAL is opening, DISTAL is closed

CONFIGURATIONS 2 > 3

7) PROXIMAL is opened and resetting, DISTAL is closed

CONFIGURATIONS 3 > 4

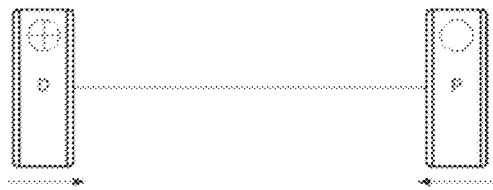

8) PROXIMAL is opened and reset, DISTAL is closed

CONFIGURATION 4

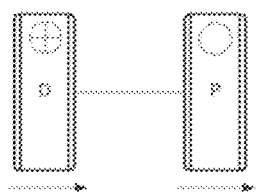

FIG. 9

1) PROXIMAL is closed, DISTAL is opening

CONFIGURATIONS 5 > 6

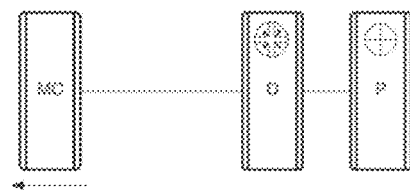

2) PROXIMAL is closed, DISTAL is opened and moving forward

CONFIGURATIONS 6 > 1

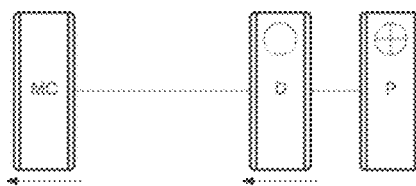

3) PROXIMAL is closed, DISTAL is opened and in position

CONFIGURATION 1

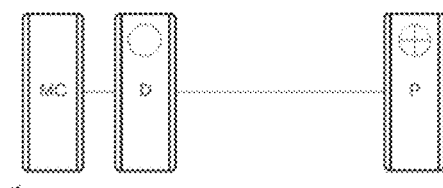

4) PROXIMAL is closed, DISTAL is closing

CONFIGURATIONS 1 > 2

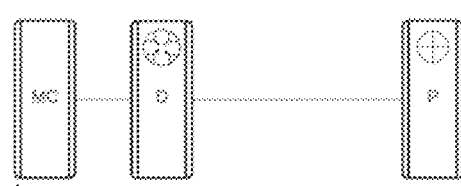

5) PROXIMAL is opening, DISTAL is closed

CONFIGURATIONS 2 > 3

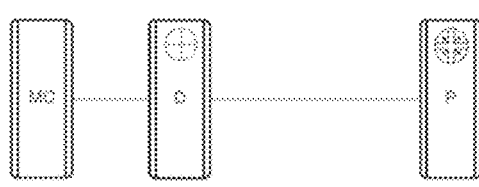

6) PROXIMAL is opened and moving forward, DISTAL is closed

CONFIGURATIONS 3 > 4

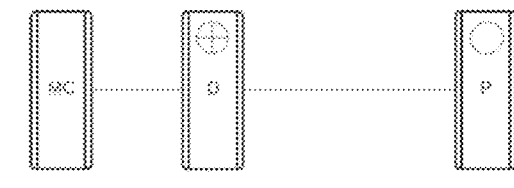

7) PROXIMAL is opened and in position, DISTAL is closed

CONFIGURATIONS 4

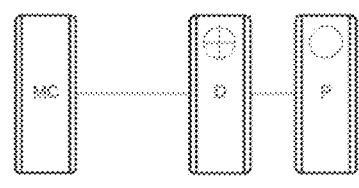

8) PROXIMAL is closing, DISTAL is closed

CONFIGURATIONS 4 > 5

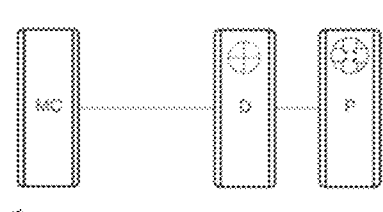

FIG. 10

1) PROXIMAL is opening, DISTAL is closed

CONFIGURATIONS 5 > 4

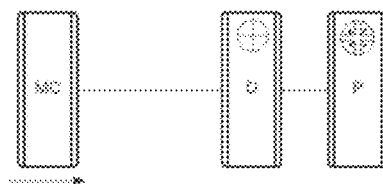

2) PROXIMAL is opened and moving to position, DISTAL is closed

CONFIGURATIONS 4 > 3

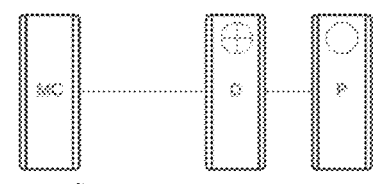

3) PROXIMAL is opened and in position, DISTAL is closed

CONFIGURATION 3

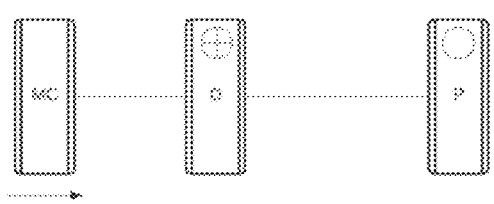

4) PROXIMAL is closing, DISTAL is closed

CONFIGURATIONS 3 > 2

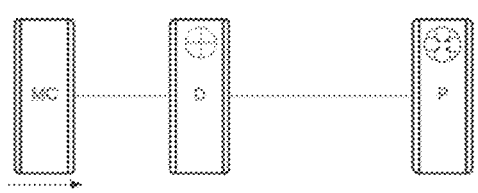

5) PROXIMAL is closed, DISTAL is opening

CONFIGURATIONS 2 > 1

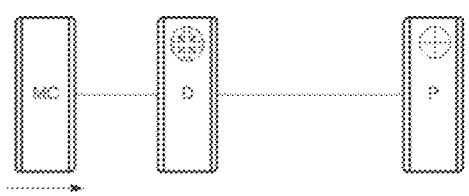

6) PROXIMAL is closed, DISTAL is opened and moving to position

CONFIGURATIONS 1 > 8

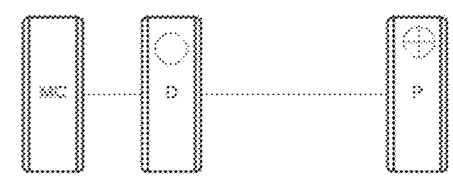

7) PROXIMAL is closed, DISTAL is opened and in position

CONFIGURATIONS 8

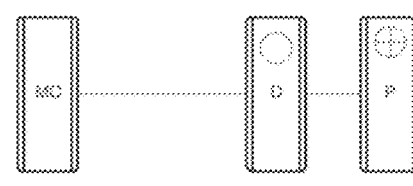

8) PROXIMAL is closed, DISTAL is closing

CONFIGURATIONS 8 > 5

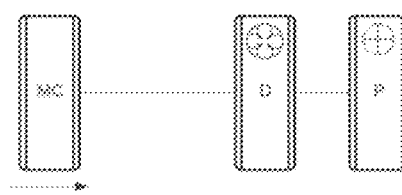

FIG. 11

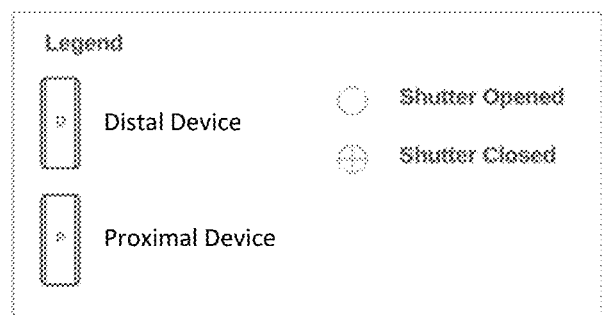
CONFIGURATION 1 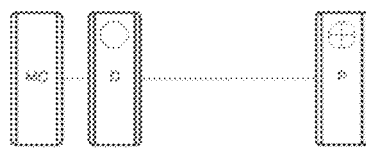
CONFIGURATION 2 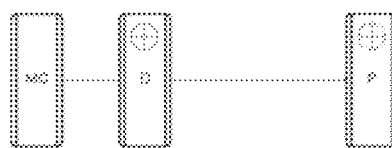
CONFIGURATION 3 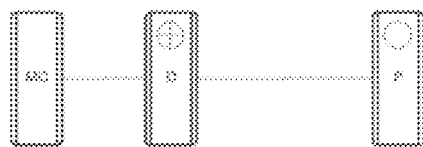
CONFIGURATION 4 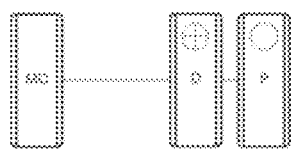
CONFIGURATION 5 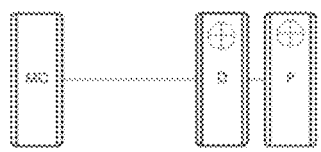
CONFIGURATION 6 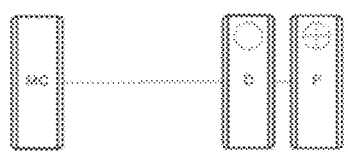
PATIENT ←
FIG. 12

SYSTEMS, METHODS, AND DEVICES FOR ADVANCING AN ENDOVASCULAR INSTRUMENT

PRIORITY APPLICATION

This application is a continuation-in-part of U.S. application Ser. No. 18/676,954, filed May 29, 2024, which claims priority to U.S. Provisional Patent Application No. 63/504,943, filed May 30, 2023, each of which is incorporated herein by reference in its entirety and for all purposes. Any and all applications for which a foreign or domestic priority claim is identified in the Application Data Sheet as filed with the present application are hereby incorporated by reference under 37 CFR 1.57.

BACKGROUND

Field

Some embodiments of the present disclosure are directed to systems, methods, and devices for robotically advancing elongate tools or endovascular instruments, such as guidewires, coils, stents, catheters, and the like.

Description

Endovascular medical procedures are common. During an endovascular procedure, a tool or medical instrument that is generally configured as a thin, flexible, elongate body is inserted into and navigated through a lumen or other cavity of the body.

In some instances, the tools or medical instruments are articulable or controllable, for example, using one or more pull wires, to allow an operator to navigate the tool or medical instrument within the body. Such navigation is often accomplished through deflection (for example, bending) of the distal tip of the tool or medical instrument.

Some tools or medical instruments are configured for manual control, for example, using knobs or levers mounted on a proximally-located handle of the tool or medical instrument. In other instances, the tools or medical instruments can be configured for robotic control, for example, control by a robotic medical system. In some embodiments, an operator can use the robotic medical system (for example, a controller, user interface, and/or the like) to robotically control the tool or medical instrument.

SUMMARY

In some aspects, a system for moving an elongate tool through a lumen is described. The system can include a proximal device and a distal device. The proximal device can be configured to move linearly in proximal and distal directions and can include a proximal clamp or shutter configured to transition between an open state in which an elongate tool moves freely through the proximal clamp and a closed state in which the elongate tool is fixedly held by the proximal clamp. The distal device can be configured to move linearly in the proximal and distal directions and can comprise a distal clamp or shutter configured to transition between an open state in which the elongate tool moves freely through the distal clamp and a closed state in which the elongate tool is fixedly held by the distal clamp. The system can also include at least one processor and at least one electronic storage medium, the at least electronic storage medium storing instructions configured to cause the at least one processor to continuously advance the elongate tool in the distal direction by transitioning the distal device and the proximal device sequentially through one or more of the following states: (1) a first state, wherein the proximal device is moving in the distal direction and the proximal clamp is closed, and the distal device is moving in the distal direction and the distal clamp is closing, (2) a second state, wherein the proximal device is moving in the distal direction and the proximal clamp is opening, and the distal device is moving in the distal direction and the distal clamp is closed, (3) a third state, wherein the proximal device is moving in the proximal direction and the proximal clamp is open, and the distal device is moving in the distal direction and the distal clamp is closed, (4) a fourth state, wherein the proximal device is moving in the distal direction and the proximal clamp is open, and the distal device is moving in the distal direction and the distal clamp is closed, (5) a fifth state, wherein the proximal device is moving in the distal direction and the proximal clamp is closing, and the distal device is moving in the distal direction and the distal clamp is closed, (6) a sixth state, wherein the proximal device is moving in the distal direction and the proximal clamp is closed, and the distal device is moving in the distal direction and the distal clamp is opening, (7) a seventh state, wherein the proximal device is moving in the distal direction and the proximal clamp is closed, and the distal device is moving in the proximal direction and the distal clamp is open, and (8) an eighth state, wherein the proximal device is moving in the distal direction and the proximal clamp is closed, and the distal device is moving the distal direction and the distal clamp is open. In some instances, the first state sequentially follows the eighth state.

In some embodiments, the system may include one or more of the following features in any combination: (a) wherein, as the distal device and the proximal device sequentially transition through one or more of the states, the elongate tool advances in a continuous manner; (b) wherein, as the distal device and the proximal device sequentially transition through one or more of the states, the elongate tool advances with a constant velocity; (c) wherein the elongate tool comprises a guidewire, a coil, a stent, a flow diverter, or a stent retriever; (d) wherein the instructions are configured to cause the at least one processor to begin advancing the elongate tool from any of the states; (e) wherein the instructions are configured to cause the at least one processor, using the proximal device and the distal device, to stop inserting the elongate tool in the distal direction, and retract the elongate tool in the proximal direction; (f) wherein retraction can begin from any of the states; (g) wherein retraction is continuous; (h) a catheter device configured to fixedly engage with a catheter, the catheter comprising a lumen with the elongate tool inserted therethrough, the catheter device configured to move linearly in proximal and distal directions, wherein the catheter device is positioned distal to the distal device; (i) wherein the instructions are further configured to cause the at least one processor to advance or retract the catheter by moving the catheter device linearly in the distal and proximal directions; (j) wherein the elongate tool extends from the lumen of the catheter, through the distal clamp of the distal device, and through the proximal clamp of the proximal device; (k) wherein the catheter comprises a microcatheter; and/or other features as described herein.

In some aspects, a system for moving an elongate tool through a lumen is described. The system can include a proximal device and a distal device. The proximal device can be configured to move linearly in proximal and distal directions and can include a proximal clamp or shutter configured to transition between an open state in which an elongate tool moves freely through the proximal clamp and a closed state in which the elongate tool is fixedly held by the proximal clamp. The distal device can be configured to move linearly in the proximal and distal directions and can include a distal clamp or shutter configured to transition between an open state in which the elongate tool moves freely through the distal clamp and a closed state in which the elongate tool is fixedly held by the distal clamp. The system can also include at least one processor and at least one electronic storage medium, the at least electronic storage medium storing instructions configured to cause the at least one processor to continuously retract the elongate tool in the proximal direction by transitioning the distal device and the proximal device sequentially through one or more the following states: (1) a first state, wherein the proximal device is moving in the proximal direction and the proximal clamp is closing, and the distal device is moving in the proximal direction and the distal clamp is closed, (2) a second state, wherein the proximal device is moving in the proximal direction and the proximal clamp is closed, and the distal device is moving in the proximal direction and the distal clamp is opening, (3) a third state, wherein the proximal device is moving in the proximal direction and the proximal clamp is closed, and the distal device is moving in the distal direction and the distal clamp is open, (4) a fourth state, wherein the proximal device is moving in the proximal direction and the proximal clamp is closed, and the distal device is moving in the proximal direction and the distal clamp is open, (5) a fifth state, wherein the proximal device is moving in the proximal direction and the proximal clamp is closed, and the distal device is moving in the proximal direction and the distal clamp is closing, (6) a sixth state, wherein the proximal device is moving in the proximal direction and the proximal clamp is opening, and the distal device is moving in the proximal direction and the distal clamp is closed, (7) a seventh state, wherein the proximal device is moving in the distal direction and the proximal clamp is open, and the distal device is moving in the proximal direction and the distal clamp is closed, and (8) an eighth state, wherein the proximal device is moving in the proximal direction and the proximal clamp is closing, and the distal device is moving in the proximal direction and the distal clamp is closed. In some instances, the first state sequentially follows the eighth state.

In some embodiments, the system may include one or more of the following features in any combination: (a) wherein, as the distal device and the proximal device sequentially transition through one or more of the states, the elongate tool retracts in a continuous manner; (b) wherein, as the distal device and the proximal device sequentially transition through one or more of the states, the elongate tool retracts with a constant velocity; (c) wherein the elongate tool comprises a guidewire, a coil, a stent, a flow diverter, or a stent retriever; (d) wherein the instructions are configured to cause the at least one processor to begin retracting the elongate tool from any of the states; (e) wherein the instructions are configured to cause the at least one processor, using the proximal device and the distal device, to stop retracting the elongate tool in the proximal direction, and insert the elongate tool in the distal direction; (f) wherein insertion can begin from any of the states; (g) wherein insertion is continuous; (h) a catheter device configured to fixedly engage with a catheter, the catheter comprising a lumen with the elongate tool inserted therethrough, the catheter device configured to move linearly in proximal and distal directions, wherein the catheter device is positioned distal to the distal device; (i) wherein the instructions are further configured to cause the at least one processor to advance or retract the catheter by moving the catheter device linearly in the distal and proximal directions; (j) wherein the elongate tool extends from the lumen of the catheter, through the distal clamp of the distal device, and through the proximal clamp of the proximal device; (k) wherein the catheter comprises a microcatheter; and/or other features as described herein.

In another aspect, a system for advancing a catheter over an elongate tool is described. The system can include a catheter device, a distal elongate tool device, and proximal elongate tool device. The catheter device can be configured to fixedly engage with a catheter. The catheter can include a lumen with an elongate tool inserted therethrough. The catheter device can be configured to move linearly in proximal and distal directions. The distal elongate tool device can be positioned proximal to the catheter device and can be configured to move linearly in the proximal and distal directions. The distal elongate tool device can include a distal clamp or shutter, wherein the elongate tool extends from the lumen of the catheter through the distal clamp, and wherein the distal clamp is configured to transition between an open state in which the elongate tool moves freely through the distal clamp and a closed state in which the elongate tool is fixedly held by the distal clamp. The proximal elongate tool device can be positioned proximal to the distal elongate tool device and can be configured to move linearly in the proximal and distal directions. The distal elongate tool device can include a proximal clamp or shutter, wherein the elongate tool extends from the distal clamp through the proximal clamp, and wherein the proximal clamp is configured to transition between an open state in which the elongate tool moves freely through the proximal clamp and a closed state in which the elongate tool is fixedly held by the proximal clamp. The system can also include at least one processor and at least one electronic storage medium, the at least electronic storage medium storing instructions configured to cause the at least one processor to advance the catheter in the distal direction while parking the elongate tool by, while continuously moving the catheter device in the distal direction, transitioning the distal elongate tool device and the proximal elongate tool device sequentially through one or more the following states: (1) a first state, wherein the proximal elongate tool device is not moving and the proximal clamp is closed, and the distal elongate tool device is not moving and the distal clamp is opening, (2) a second state, wherein the proximal elongate tool device is not moving and the proximal clamp is closed, and the distal elongate tool device is moving in the distal direction and the distal clamp is open, (3) a third state, wherein the proximal elongate tool device is not moving and the proximal clamp is closed, and the distal elongate tool device is not moving and the distal clamp is open, (4) a fourth state, wherein the proximal elongate tool device is not moving and the proximal clamp is closed, and the distal elongate tool device is not moving and the distal clamp is closing, (5) a fifth state, wherein the proximal elongate tool device is not moving and the proximal clamp is opening, and the distal elongate tool device is not moving and the distal clamp is closed, (6) a sixth state, wherein the proximal elongate tool device is moving in the distal direction and the proximal clamp is open, and the distal elongate tool device is not moving and the distal clamp is closed, (7) a seventh state, wherein the proximal elongate tool device is not moving and the proximal clamp is open, and the distal elongate tool device is not moving and the distal clamp is closed, and (8) an eighth state, wherein the proximal elongate tool device is not moving and the proximal clamp is closed, and the distal elongate tool device is not moving and the distal clamp is opening. In some instances, the first state sequentially follows the eighth state.

The system can include one or more of the following features in any combination: (a) wherein the elongate tool comprises a guidewire, a coil, a stent, a flow diverter, or stent retriever; (b) wherein the catheter comprises an elongate body and the lumen is formed through the elongate body; (c) wherein the catheter comprises a microcatheter; (d) wherein the catheter is steerable; (e) wherein the catheter is advanced continuously over the elongate tool; (f) wherein the elongate tool does not advance or retract; (g) wherein the instructions are configured to cause the at least one processor, using the catheter device, the proximal elongate tool device and the distal elongate tool device, to stop inserting the catheter over the elongate tool in the distal direction, and retract the catheter over the elongate tool in the proximal direction; (h) wherein the elongate tool does not advance or retract during retraction of the catheter; (i) wherein the instructions are configured to cause the at least one processor, using the catheter device, the proximal elongate tool device and the distal elongate tool device, to insert or retract the elongate tool in the distal or proximal directions in a continuous manner; and/or other features as described herein.

In another aspect, a system for retracting a catheter over an elongate tool is described. The system can include a catheter device, a distal elongate tool device, and proximal elongate tool device. The catheter device can be configured to fixedly engage with a catheter. The catheter can include a lumen with an elongate tool inserted therethrough. The catheter device can be configured to move linearly in proximal and distal directions. The distal elongate tool device can be positioned proximal to the catheter device and can be configured to move linearly in the proximal and distal directions. The distal elongate tool device can include a distal clamp or shutter, wherein the elongate tool extends from the lumen of the catheter through the distal clamp, and wherein the distal clamp is configured to transition between an open state in which the elongate tool moves freely through the distal clamp and a closed state in which the elongate tool is fixedly held by the distal clamp. The proximal elongate tool device can be positioned proximal to the distal elongate tool device and can be configured to move linearly in the proximal and distal directions. The distal elongate tool device can include a proximal clamp or shutter, wherein the elongate tool extends from the distal clamp through the proximal clamp, and wherein the proximal clamp is configured to transition between an open state in which the elongate tool moves freely through the proximal clamp and a closed state in which the elongate tool is fixedly held by the proximal clamp. The system can include at least one processor and at least one electronic storage medium, the at least electronic storage medium storing instructions configured to cause the at least one processor to retract the catheter in the proximal direction while parking the elongate tool by, while continuously moving the catheter device in the proximal direction, transitioning the distal elongate tool device and the proximal elongate tool device sequentially through one or more the following states: (1) a first state, wherein the proximal elongate tool device is not moving and the proximal clamp is opening, and the distal elongate tool device is not moving and the distal clamp is closed, (2) a second state, wherein the proximal elongate tool device is moving proximally and the proximal clamp is open, and the distal elongate tool device is not moving and the distal clamp is closed, (3) a third state, wherein the proximal elongate tool device is not moving and the proximal clamp is open, and the distal elongate tool device is not moving and the distal clamp is closed, (4) a fourth state, wherein the proximal elongate tool device is not moving and the proximal clamp is closing, and the distal elongate tool device is not moving and the distal clamp is closed, (5) a fifth state, wherein the proximal elongate tool device is not moving and the proximal clamp is closed, and the distal elongate tool device is not moving and the distal clamp is opening, (6) a sixth state, wherein the proximal elongate tool device is not moving and the proximal clamp is closed, and the distal elongate tool device is moving in the proximal direction and the distal clamp is open, (7) a seventh state, wherein the proximal elongate tool device is not moving and the proximal clamp is closed, and the distal elongate tool device is not moving and the distal clamp is open, and (8) an eighth state, wherein the proximal elongate tool device is not moving and the proximal clamp is closed, and the distal elongate tool device is not moving and the distal clamp is closed. In some embodiments, the first state sequentially follows the eighth state.

In some embodiments, the system can include one or more of the following features in any combination: (a) wherein the elongate tool comprises a guidewire, a coil, a stent, a flow diverter, or a stent retriever; (b) wherein the catheter comprises an elongate body and the lumen is formed through the elongate body; (c) wherein the catheter comprises a microcatheter; (d) wherein the catheter is steerable; (e) wherein the catheter is retracted continuously over the elongate tool; (f) wherein the elongate tool does not advance or retract; (g) wherein the instructions are configured to cause the at least one processor, using the catheter device, the proximal elongate tool device and the distal elongate tool device, to stop retracting the catheter over the elongate tool in the proximal direction, and insert the catheter over the elongate tool in the distal direction; (h) wherein the elongate tool does not advance or retract during insertion of the catheter; (i) wherein the instructions are configured to cause the at least one processor, using the catheter device, the proximal elongate tool device and the distal elongate tool device, to insert or retract the elongate tool in the distal or proximal direction in a continuous manner; and/or other features as described herein.

In some aspects, a system for advancing an elongate body (such as a guidewire) through a lumen is described. The system includes a first advancement device and a second advancement device. The first advancement device is configured to move between a first position and a second position a distance from the first position, wherein the first position is proximal to the second position. The first advancement device includes a first clamp or shutter configured to move between an open configuration and a closed configuration, wherein the first clamp is configured to contact or fixedly engage the guidewire when the first clamp is in the closed configuration. The second advancement device is positioned between the first advancement device and an access point to the lumen. The second advancement device includes a second clamp configured to move between an open configuration and a closed configuration, wherein the second clamp is configured to contact or fixedly engage the guidewire when the second clamp is in the closed configuration. The first advancement device is configured to move from the first position to the second position when the first clamp is in the closed configuration to advance the guidewire the distance through the lumen.

In some embodiments, the system includes one or more of the following features in any combination: (a) wherein the first advancement device is coupled to a rail system, wherein the rail system is configured to move the first advancement device between the first position and the second position; (b) wherein the second advancement device is coupled to a catheter (such as a microcatheter), and wherein the guidewire is inserted through the catheter; (c) wherein the second advancement device is configured to move between a third position and a fourth position the distance from the third position, wherein the third position is proximal to the fourth position, and wherein second advancement device is configured to move from the third position to the fourth position to advance the microcatheter through the lumen; (d) wherein the second clamp is in the open configuration when the first advancement device moves from the first position to the second position; (e) wherein the first clamp is configured to move from the closed configuration to the open configuration after the first advancement device moves from the first position to the second position, and wherein the second clamp is configured to move from the open configuration to the closed configuration after the first advancement device moves from the first position to the second position; (f) wherein the first advancement device is configured to move from the second position to the first position when the first clamp is in the open configuration; (g) wherein the distance is between about 20 mm and about 60 mm; and/or other features as described herein.

In some aspects, a tool advancement device is described. The tool advancement device can include a housing comprising a first recess and a first gear positioned in the first recess, the first gear configured to rotate in a first direction around an elongate tool (such as a guidewire) and a second direction around the guidewire, the second direction opposite the first direction. The first gear can include a second recess. The device can also include a first collet clamp positioned in the second recess, the first collet clamp configured to rotate with the first gear, the first collet clamp comprising a third recess, the third recess comprising internal threading. The device can also include a second gear positioned in the first recess, the second gear configured to rotate in the first direction and the second direction. The device can also include a first input configured to rotate the first gear in the first direction and the second direction and a second input configured to rotate the second gear in the first direction and the second direction. The device can also include a second collet clamp comprising a fourth recess, and external threading configured to interact with the internal threading of the first collet clamp, wherein the second collet clamp is configured to extend into the third recess of the first collet clamp. The device can also include a collet positioned in the fourth recess of the second collet clamp, the collet configured to move between an open configuration and a closed configuration, wherein the collet contact a guidewire when the collet is in the closed configuration. The internal threading and the external threading can be configured to translate the first collet clamp towards the second collet clamp to move the collet to the closed configuration when the first gear is rotated relative to the second gear in the first direction, and wherein the internal threading and the external threading are configured to translate the first collet clamp away from the second collet clamp to move the collet to the open configuration when the first gear is rotated relative to the second gear in the second direction.

In some embodiments, the device can include one or more of the following features in any combination: (a) wherein the second gear is positioned proximal to the first gear, and wherein the second collet clamp is positioned in a fifth recess of the second gear; (b) wherein when the collet is in the closed configuration, the collet is configured to rotate the guidewire when the first gear and the second gear are rotated in the first direction or the second direction; (c) wherein the first gear is rotated in the first direction and the second gear is rotated in the second direction to rotate the first gear relative to the second gear in the first direction, and wherein the wherein the first gear is rotated in the second direction and the second gear is rotated in the first direction to rotate the first gear relative to the second gear in the second direction; (d) wherein the second collet clamp is coupled to the housing; (e) wherein the second gear is positioned distal to the first gear, and wherein the second gear comprises a fifth recess, the fifth recess configured extend distally from the first recess of the housing, wherein the fifth recess is configured to receive a microcatheter positioned over the guidewire; (f) wherein the second gear is configured to rotate the microcatheter in the first direction when the second gear rotates in the first direction, and wherein the second gear is configured to rotate the microcatheter is the second direction when the second gear rotates in the second direction; and/or other features as described herein.

In another aspect, a method for advancing an elongate tool (such as a guidewire) through a lumen can include the steps of: inserting a guidewire through a first advancement device and a second advancement device, wherein the second advancement device is positioned between the first advancement device and an access point to a lumen; moving the first advancement device to a closed configuration, wherein the first advancement device contacts or fixedly engages the guidewire when the first advancement device is in the closed configuration; and moving the first advancement device from a first position to a second position to advance the guidewire a distance through the lumen, wherein the second position is the distance from the first position between the first position and the access point.

In some embodiments, the method can include one or more of the following features in any combination: (a) moving the first advancement device to an open configuration after the first tool advancement device moves from the first position to the second position so the first tool advancement device does not contact the guidewire; (b) moving the second advancement device to the closed configuration; (c) moving the first advancement device from the second position to the first position; (d) moving the first advancement device to the closed configuration and the second advancement device to the open configuration; (e) wherein the guidewire is inserted through a catheter (such as a microcatheter), and the second advancement device is coupled to the catheter; (f) moving the second advancement device from a third position to a fourth position to advance the catheter through the lumen, wherein the fourth position in between the third position and the access point; (g) wherein the distance is between about 20 mm and about 60 mm; and/or other features as described herein.

BRIEF DESCRIPTION OF THE DRAWINGS

Various embodiments are depicted in the accompanying drawings for illustrative purposes and should in no way be interpreted as limiting the scope of the embodiments. It is to be understood that the attached drawings are for the purpose of illustrating concepts disclosed in the present application and may not be to scale. Furthermore, various features of different disclosed embodiments can be combined to form additional embodiments, which are part of this disclosure.

FIGS. 1A-1B illustrate an example system for advancing a guidewire through a patient lumen.

FIGS. 5A-5D illustrate various views of a first tool advancement device according to some embodiments described herein.

FIGS. 5E-5H illustrate various views of a second tool advancement device according to some embodiments described herein.

FIG. 8 illustrates various sequential states for a proximal device and a distal device to insert an elongate tool in a continuous manner.

FIG. 9 illustrates various sequential states for a proximal device and a distal device to retract an elongate tool in a continuous manner.

FIG. 10 illustrates various sequential states for a catheter device, a proximal elongate tool device, and a distal elongate tool device to insert a catheter while parking the elongate tool device.

FIG. 11 illustrates various sequential states for a catheter device, a proximal elongate tool device, and a distal elongate tool device to retract a catheter while parking the elongate tool device.

FIG. 12 illustrates various configurations for a catheter device, a proximal elongate tool device, and a distal elongate tool device, which are referenced in FIGS. 8-11.

DETAILED DESCRIPTION

Although several embodiments, examples, and illustrations are disclosed below, it will be understood by those of ordinary skill in the art that the system, methods, and devices described herein extend beyond the specifically disclosed embodiments, examples, and illustrations and include other uses of the system, methods, and devices and modifications and equivalents thereof. Embodiments of the disclosure are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the disclosure. In addition, embodiments of the disclosure can comprise several novel features and no single feature is solely responsible for its desirable attributes or is essential to practicing the system, methods, and devices herein described.

Figure 1A:
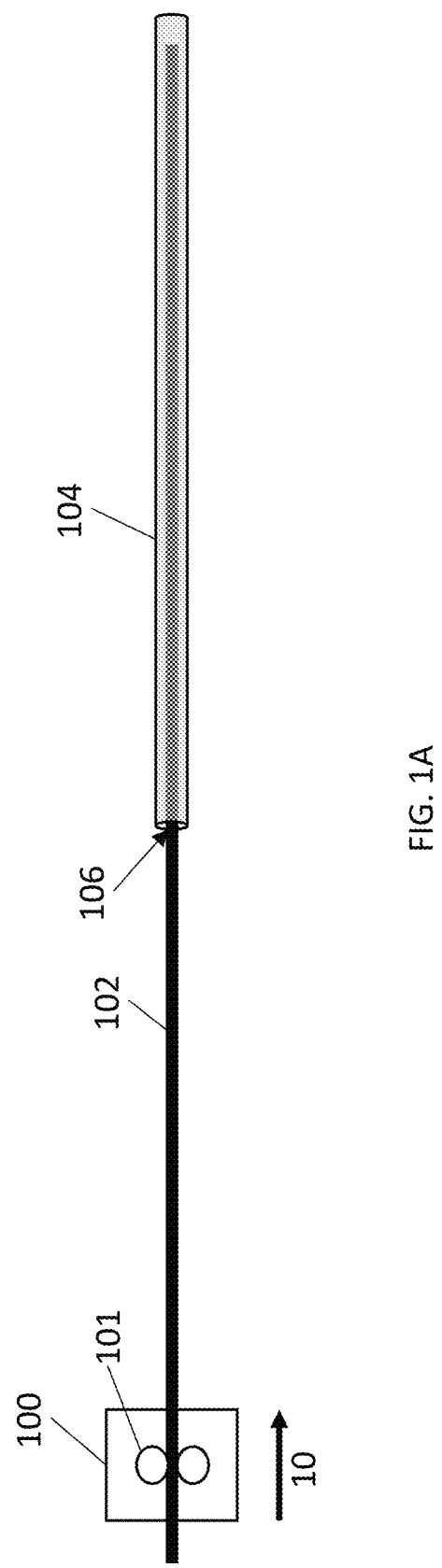

An elongate body or endovascular tool 102 (for example, a guidewire, a coil, a stent, a flow diverter, a stent retriever, or the like) may be inserted into a lumen 104 via a remotely controlled system 100, as shown in FIG. 1A. The lumen 104 can be, for example, a lumen formed through another endovascular tool such as a catheter or a patient lumen. The endovascular tool 102 be inserted into the lumen 104 through an access point 106. In order to advance the endovascular tool 102 through the patient lumen 104, the system 100 may apply an axial force 10 to the endovascular tool 102 at a point of application outside of the lumen 104. In some instances, the system 100 may include rollers 101 configured to apply the axial force 10 to the endovascular tool 102. The rollers 101 may be configured to rotate in order to apply the axial force 10 to the endovascular tool 102. In other embodiments, rollers 101 may be replaced with a clamping mechanism that clamps onto the endovascular tool and then moves backwards and forwards to advance the endovascular tool 102.

In order to navigate through the anatomical luminal networks, the endovascular tool 102 may have a small diameter, for example, between about 0.010 inches and about 0.038 inches, and may be generally flexible. Accordingly, when the system 100 applies the axial force 10 to the endovascular tool 102, the endovascular tool 102 may deform, bend, or buckle between the point of application of the axial force 10 and the access point 106, as shown in FIG. 1B. Additionally, when the rollers 101 rotate, due to the small diameter of the endovascular tool 102, the rollers 101 may slip and not apply the axial force 10 to the endovascular tool 102 preventing or inhibiting the system 100 from precisely controlling advancement of the endovascular tool 102. These problems can be overcome using the systems described below.

Figure 2A:
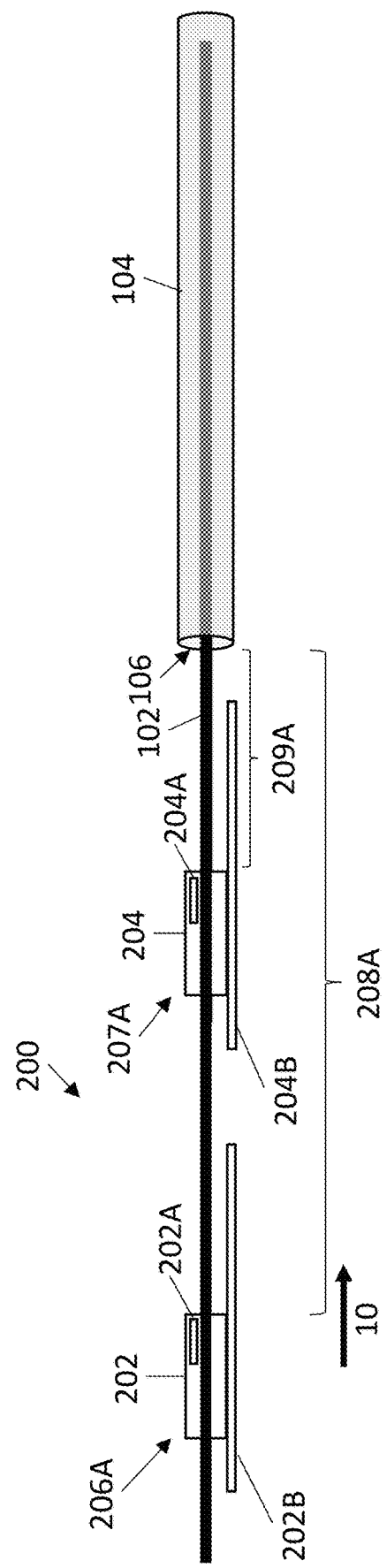
FIGS. 2A-2C illustrate another system for advancing a guidewire through a patient lumen according to some embodiments described herein.
Figure 2B:
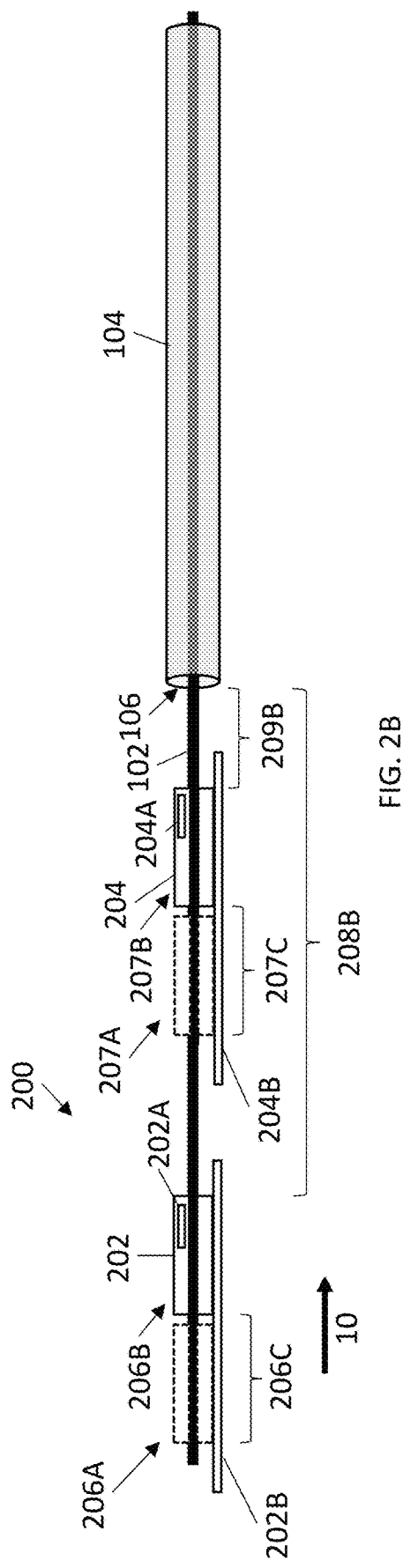
Figure 2C:
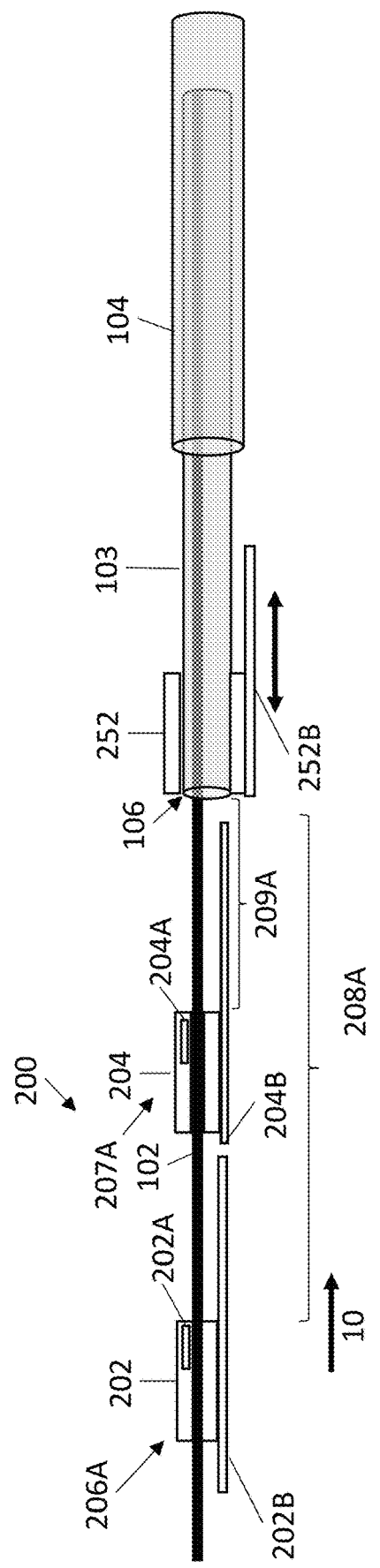

FIGS. 2A-2C show a system 200 for advancing an elongate body or endovascular tool 102 (such as a guidewire, a coil, a stent, a flow diverter, a stent retriever, or the like) through a patient lumen 104. In some embodiments, the endovascular tool 102 may be advanced through the patient lumen 104 with a catheter 103, as shown in FIG. 2C. In some embodiments, the system 200 may include a first tool advancement device 202 (e.g., a proximal device or proximal elongate tool device) and a second tool advancement device 204 (e.g. a distal device or a distal elongate tool device). In some embodiments, the second tool advancement device 204 may be positioned between the first tool advancement device 202 and an access point 106 to the patient lumen 104. In some embodiments, the first tool advancement device 202 may be positioned proximal to the second tool advancement device 204 and/or the access point 106. In some embodiments, the second tool advancement device 204 may be positioned distal to the first tool advancement device 202 and/or proximal to the access point 106.

In some embodiments, the first tool advancement device 202 and/or the second tool advancement device 204 may be configured to move or transition (e.g., open and close) between an open configuration and a closed configuration. For example, each of the first tool advancement device 202 and the second tool advancement device 204 can include a clamp or shutter that transitions between an open configuration that does not clamp on the endovascular tool 102 and a closed configuration that clamps, secures, or fixedly engages the endovascular tool 102. In some embodiments, the first tool advancement device 202 may include an actuator 202A configured to move the first tool advancement device 202 (e.g., the clamp or shutter thereof) between the open configuration and the closed configuration, and the second tool advancement device 204 may include an actuator 204A configured to move the second tool advancement device 204 (e.g., the clamp or shutter thereof) between the open configuration and the closed configuration.

In some embodiments, when the first tool advancement device 202 is in the closed configuration, the first tool advancement device 202 may contact or fixedly engage with the endovascular tool 102 and/or apply a force to the endovascular tool 102. In some embodiments, when the first tool advancement device 202 is in the open configuration, the first tool advancement device 202 may not contact or may allow the endovascular tool 102 to move freely or relatively freely through the first tool advancement device 202.

In some embodiments, when the second tool advancement device 204 is in the closed configuration, the second tool advancement device 204 may contact or fixedly engage with the endovascular tool 102 and/or apply the force to the endovascular tool 102, as shown in FIGS. 2A and 2B. In some embodiments, when the second tool advancement device 204 is in the open configuration, the second tool advancement device 204 may not contact or may allow the endovascular tool 102 to move freely or relatively freely through the second tool advancement device 204.

In some embodiments, the first tool advancement device 202 (or at least a portion thereof) may be configured to move linearly in proximal and distal directions. For example, as illustrated in FIG. 2B, the first tool advancement device 202 can be configured to move between a first position 206A and a second position 206B. When the first tool advancement device 202 is positioned at the first position 206A, the first tool advancement device 202 may be positioned a first distance 208A from the access point 106. When the first tool advancement device 202 is positioned at the second position 206B, the first tool advancement device 202 may be positioned a second distance 208B from the access point 106. In some embodiments, the first distance 208A may be larger than the second distance 208B. Accordingly, when the first tool advancement device 202 is positioned at the first position 206A, the first tool advancement device 202 may be further away from the access point 106 than when the first tool advancement device 202 is positioned at the second position 206B. The first tool advancement device 202 may move away (i.e., further) from the access point 106 when the first tool advancement device 202 moves from the second position 206B to the first position 206A. The first tool advancement device 202 may move towards (i.e., closer to) the access point 106 when the first tool advancement device 202 moves from the first position 206A to the second position 206B.

In some embodiments, the first tool advancement device 202 may include or be mounted on a rail or linear movement system 202B. The first tool advancement device 202 may translate along the rail system 202B to move between the first position 206A and the second position 206B.

In some embodiments, the first tool advancement device 202 may be configured to advance the endovascular tool 102 through the patient lumen 104 and/or through the lumen of the catheter 103 as shown in FIG. 2C. In some embodiments, if the first tool advancement device 202 is not positioned at the first position 206A, the first tool advancement device 202 may move to the first position 206A. The first tool advancement device 202 may be in the open configuration when the first tool advancement device 202 moves to the first position 206A so the first tool advancement device 202 does not contact the endovascular tool 102 and/or retract the endovascular tool 102 from the patient lumen 104. In some embodiments, the first tool advancement device 202 may move from the closed configuration to the open configuration before the first tool advancement device 202 moves to the first position 206A. In some embodiments, the actuator 202A may move the first tool advancement device 202 from the closed configuration to the open configuration.

In some embodiments, the first tool advancement device 202 may move from the open configuration to the closed configuration when the first tool advancement device 202 is positioned at the first position 206A. In some embodiments, the actuator 202A may move the first tool advancement device 202 from the open configuration to the closed configuration.

In some embodiments, the first tool advancement device 202 may move from the first position 206A to the second position 206B when the first tool advancement device 202 is in the closed configuration to advance the endovascular tool 102 through the patient lumen 104, as shown in FIG. 2B. In some embodiments, the first tool advancement device 202 may advance the endovascular tool 102 a distance through the patient lumen 104 and/or through the catheter 103. In some embodiments, the distance may include a distance 206C between the first position 206A and the second position 206B. In some embodiments, the distance 206C may include a distance of about 1 mm, 2 mm, 3 mm, 4 mm, 5 mm, 10 mm, 15 mm, 20 mm, 25 mm, 30 mm, 35 mm, 40 mm, 45 mm, 50 mm, 55 mm, 60 mm, 65 mm, 70 mm, 75 mm, 80 mm, 85 mm, 90 mm, 95 mm, 100 mm, and/or any value between the aforementioned values. In some embodiments, the distance 206C may include a distance between about 10 mm and about 70 mm. In some embodiments, the distance 206C may include a distance between about 20 mm and about 60 mm. In some embodiments, the distance 206C may include a distance between about 30 mm and about 50 mm.

In some embodiments, the first tool advancement device 202 may apply the axial force 10 to the endovascular tool 102 via the clamp or shutter between the first tool advancement device 202 and the endovascular tool 102 generated by the force applied to the endovascular tool 102 by the first tool advancement device 202. The axial force 10 applied to the endovascular tool 102 by the first tool advancement device 202 may secure the endovascular tool 102 to the first tool advancement device 202 as the first tool advancement device 202 moves linearly in the distal direction to advance the endovascular tool 102 through the patient lumen 104 and/or catheter 103.

In some embodiments, after the first tool advancement device 202 moves to the second position 206B, the first tool advancement device 202 may move from the closed configuration to the open configuration and/or the actuator 202A may move the first tool advancement device 202 from the closed configuration to the open configuration. In some embodiments, after the first tool advancement device 202 moves from the closed configuration to the open configuration, the first tool advancement device 202 may move from the second position 206B to the first position 206A, as described above.

In some embodiments, the second tool advancement device 204 may contact the endovascular tool 102 when the second tool advancement device 204 is in the closed configuration, as shown in FIG. 2A. The second tool advancement device 204 may be in the closed configuration when the first tool advancement device 202 moves from the second position 206B to the first position 206A (e.g., away from the second tool advancement device 204). In some embodiments, if the second tool advancement device 204 is in the open configuration when the first tool advancement device 202 is in the second position 206B, the second tool advancement device 204 may move to the closed configuration and/or the actuator 204A may move the second tool advancement device 204 to the closed configuration. In some embodiments, the second tool advancement device 204 may move to the closed configuration and/or the actuator 204A may move the second tool advancement device 204 to the closed configuration before the first tool advancement device 202 moves from the second position 206B to the first position 206A.

In some embodiments, as described above, the second tool advancement device 204 may apply the force to the endovascular tool 102 when the second tool advancement device 204 is in the closed configuration. When the first tool advancement device 202 moves from the second position 206B to the first position 206A, if the first tool advancement device 202 contacts the endovascular tool 102, the second tool advancement device 204 may prevent or inhibit the first tool advancement device 202 from removing the endovascular tool 102 from the patient lumen 104 and/or catheter 103.

In some embodiments, the second tool advancement device 204 may move from the closed configuration to the open configuration and/or the actuator 204A may move the second tool advancement device 204 from the closed configuration to the open configuration when the first tool advancement device 202 is in the first position. In some embodiments, after the first tool advancement device 202 moves to the first position 206A, the second tool advancement device 204 may move from the closed configuration to the open configuration and/or the actuator 204A may move the second tool advancement device 204 from the closed configuration to the open configuration.

In some embodiments, as shown for example in FIG. 2B, the second tool advancement device 204 may be configured to move between a first position 207A and a second position 207B. When the second tool advancement device 204 is positioned at the first position 207A, the second tool advancement device 204 may be positioned a first distance 209A from the access point 106. When the second tool advancement device 204 is positioned at the second position 207B, the second tool advancement device may be positioned a second distance 209B from the access point 106. In some embodiments, the first distance 209A may be larger than the second distance 209B. Accordingly, when the second tool advancement device 204 is positioned at the first position 207A, the second tool advancement device 204 may be further away from the access point 106 than when the second tool advancement device 204 is positioned at the second position 207B. The second tool advancement device 204 may move away (i.e., further) from the access point 106 when the second tool advancement device 204 moves from the second position 207B to the first position 207A. The second tool advancement device 204 may move towards (i.e., closer to) the access point 106 when the second tool advancement device 204 moves from the first position 207A to the second position 207B.

In some embodiments, a distance 207C between the first position 207A of the second tool advancement device 204 and the second position 207B of the second tool advancement device 204 may include a distance longer than the distance 206C between the first position 206A of the first tool advancement device 202 and the second position 206B of the first tool advancement device 202. In some embodiments, the distance 207C may include a distance shorter than the distance 206C. In some embodiments, the distance 207C may include a same distance as the distance 206C.

In some embodiments, the second tool advancement device 204 may include a rail system or linear movement system 204B. The second tool advancement device 204 may translate along the rail system 204B to move between the first position 207A and the second position 207B.

In some embodiments, the second tool advancement device 204 (or at least a portion thereof) may be configured to move from the first position 207A to the second position 207B to advance the endovascular tool 102 though the patient lumen 104, as shown in FIG. 2B and/or catheter 103 as shown in FIG. 2C. In some embodiments, the second tool advancement device 204 may be configured to move from the first position 207A to the second position 207B to advance the microcatheter 103 through the patient lumen 104 and/or catheter 103.

In some embodiments, the second tool advancement device 204 may be configured to move from the first position 207A to the second position 207B when the first tool advancement device 202 moves from the first position 206A to the second position 206B. In some embodiments, as shown in FIG. 2B, the first tool advancement device 202 and the second tool advancement device 204 may advance the endovascular tool 102 through the patient lumen 104.

In some embodiments, when the second tool advancement device 204 is positioned at the first position 207A, the second tool advancement device 204 may be in the closed configuration. If the second tool advancement device 204 is in the open configuration, the second tool advancement device 204 may move to the closed configuration and/or the actuator 204A may move the second tool advancement device 204 to the closed configuration. In some embodiments, the second tool advancement device 204 may move from the first position 207A to the second position 207B when the second tool advancement device 204 is in the closed configuration.

In some embodiments, the second tool advancement device 204 may apply the axial force 10 to the endovascular tool 102 via the shutter or clamp of the second tool advancement device 204. The axial force 10 applied to the endovascular tool 102 by the second tool advancement device 204 may cause the endovascular tool 102 to be retained by the second tool advancement device as linear movement of the second tool advancement device 204 moves the endovascular tool 102 through the patient lumen 104 and/or catheter 103.

In some embodiments, after the second tool advancement device 204 moves to the second position 207B, the second tool advancement device 204 may move from the closed configuration to the open configuration and/or the actuator 204A may move the second tool advancement device 204 from the closed configuration to the open configuration. In some embodiments, the after the second tool advancement device 204 moves from the closed configuration to the open configuration, the second tool advancement device 204 may move from the second position 207B to the first position 207A.

In some embodiments, the first tool advancement device 202 and/or the second tool advancement device 204 may be configured to rotate the endovascular tool 102. The first tool advancement device 202 and/or the second tool advancement device 204 may be configured to rotate the endovascular tool 102 around an axis that may extend along a length of the endovascular tool 102. In some embodiments, the first tool advancement device 202 and/or the second tool advancement device 204 may be configured to rotate in order to rotate, roll, twist, and/or torque the endovascular tool 102 and/or the catheter 103.

In some embodiments, as shown in FIG. 2C, the endovascular tool 102 may be advanced through the patient lumen 104 in or through a catheter 103. The catheter 103 can comprise an elongate body having a lumen formed therethrough. The endovascular tool 102 can be received through the lumen of the catheter 103. As shown in FIG. 2C, the catheter 103 may be engaged with a catheter device 252. In the illustrated embodiment, the catheter device 252 engages with a proximal end of the catheter 103. The catheter device 252 can be fixedly engaged with the catheter 103. In some embodiments, the catheter device 252 can be configured to cause insertion and/or retraction of the catheter 103 in the distal and proximal direction. For example, the catheter device, in some embodiments, can be configured to move linearly in the distal and proximal directions to insert or retract the catheter 103. In the illustrated embodiment, the catheter device 252 is mounted on and configured to move linearly along a rail 252B, although other methods for linearly moving the catheter device 252B are possible. In other embodiments, the catheter device 252 can comprise a feeder that remains stationary and feeds the catheter 103 in the proximal and distal directions, for example, using one or more rollers.

Figure 3A:
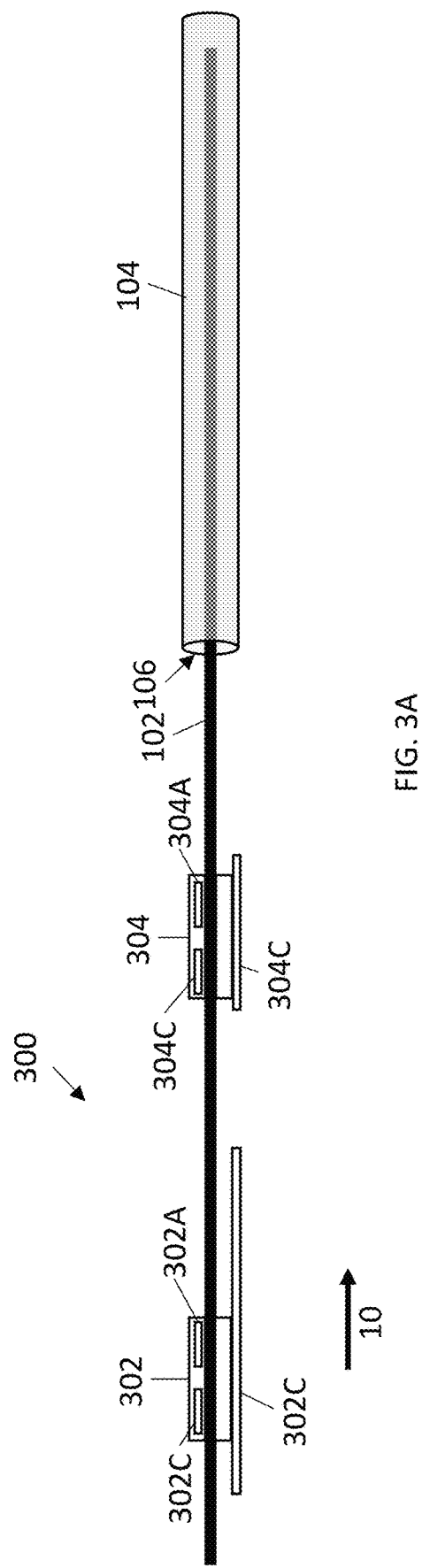
FIGS. 3A-3B illustrate another system for advancing a guidewire through a patient lumen according to some embodiments described herein.
Figure 3B:
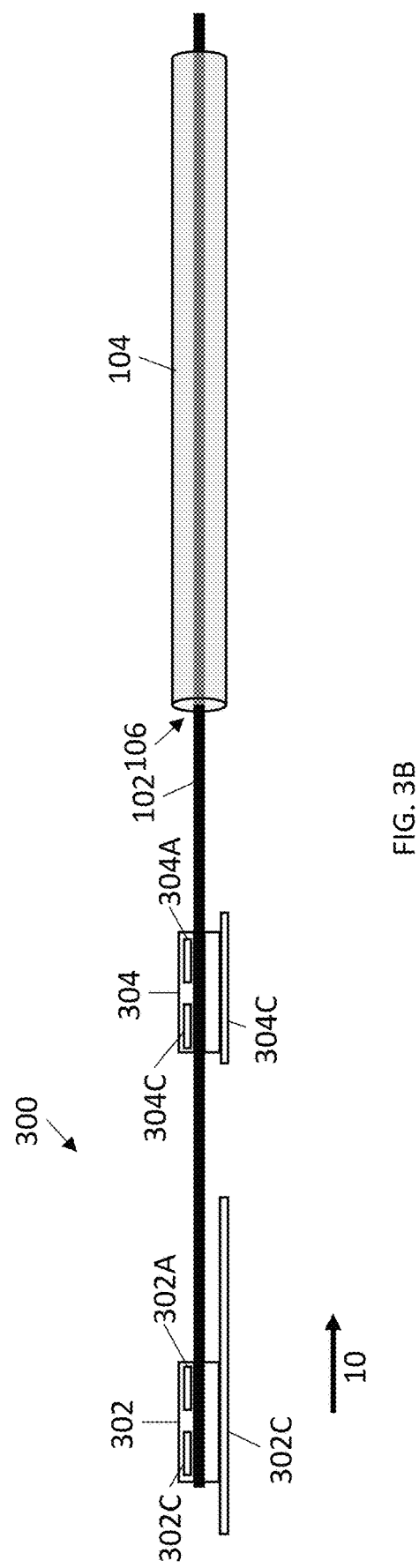

FIGS. 3A-3B show a system 300 for advancing an endovascular tool 102 through a patient lumen 104. Common features between the system 200 and the system 300 will not be described again but are incorporated here in their entirety. The system 300 may include a first tool advancement device 302 and a second tool advancement device 304. In some embodiments, the first tool advancement device 302 may include a rail system 302B and the second tool advancement device 304 may include a rail system 304B. In some embodiments, the first tool advancement device 302 includes an advancement mechanism 302C and the second tool advancement device 304 may include an advancement mechanism 304C. In some embodiments, the advancement mechanisms 302C, 304C may include a clamp or shutter that is configured to move or transition (e.g., open and close) between an open configuration and a closed configuration. In some embodiments, the first tool advancement device 302 may include an actuator 302A configured to move the advancement mechanism 302C between the open configuration and the closed configuration, and the second tool advancement device 304 may include an actuator 304A configured to move the advancement mechanism 304C between the open configuration and the closed configuration.

In some embodiments, when the advancement mechanism 302C of the first tool advancement device 302 is in the open configuration, the advancement mechanism 302C may not contact or fixedly engage with the endovascular tool 102. In some embodiments, when the advancement mechanism 304C of the second tool advancement device 304 is in the open configuration the advancement mechanism 204C may not contact or fixedly engage with the endovascular tool 102.

In some embodiments, as shown in FIGS. 3A and 3B, when the advancement mechanism 302C of the first tool advancement device 302 and/or the advancement mechanism 304C of the second tool advancement device 304 are in the closed configuration, the advancement mechanism 302C of the first tool advancement device 302 and/or the advancement mechanism 304C of the second tool advancement device 304 may contact or fixedly engage with the endovascular tool 102 and/or apply the force to the endovascular tool 102. In some embodiments, when the advancement mechanism 302C of the first tool advancement device 302 and/or the advancement mechanism 304C of the second tool advancement device 304 are in the closed configuration, the advancement mechanisms 302C, 304C may apply the axial force 10 to the endovascular tool 102 in order to advance the endovascular tool 102 through the patient lumen 104 and/or catheter 103.

In some embodiments, after the advancement mechanism 302C of the first tool advancement device 302 and/or the advancement mechanism 304C of the second tool advancement device 304 advance the endovascular tool 102 through the patient lumen 104, the advancement mechanism 302C of the first tool advancement device 302 and/or the advancement mechanism 304C of the second tool advancement device 304 may move to the open configuration.

In some embodiments, the advancement mechanism 304C of the second tool advancement device 302 may be in the open configuration when the advancement mechanism 302C of the first tool advancement device 302 advances the endovascular tool 102 through the patient lumen 104. In some embodiments, after the advancement mechanism 302C of the first tool advancement device 302 advances the endovascular tool 102 through the patient lumen 104, the advancement mechanism 304C of the second tool advancement device 304 may move to the closed configuration to apply the force to the endovascular tool 102 and/or the advancement mechanism 302C of the first tool advancement device 302 may move to the open configuration. In some embodiments, when the advancement mechanism 302C of the first tool advancement device 302 is in the open configuration the advancement mechanism 302C of the first tool advancement device 302 may move, translate, or otherwise reset in order to prepare to advance the endovascular tool 102 further though the patient lumen 104. In some embodiments, the force applied to the endovascular tool 102 by the advancement mechanism 304C of the second tool advancement device 304 may prevent or inhibit the advancement mechanism 302C of the first tool advancement device 302 from removing the endovascular tool 102 from the patient lumen 104.

In some embodiments, the advancement mechanism 302C of the first tool advancement device 302 and the advancement mechanism 304C of the second tool advancement device 304 may advance the endovascular tool 102 through the patient lumen 104. In some embodiments, both the advancement mechanism 302C of the first tool advancement device 302 and the advancement mechanism 304C of the second tool advancement device 304 may advance the endovascular tool 102 through the patient lumen 104 simultaneously. In some embodiments, the advancement mechanism 302C of the first tool advancement device 302 may advance the endovascular tool 102 through the patient lumen 104 when the advancement mechanism 304C of the second tool advancement device 304 prepares to advance the endovascular tool 102 through the patient lumen 104, and/or the advancement mechanism 304C of the second tool advancement device 304 may advance the endovascular tool 102 through the patient lumen 104 when the advancement mechanism 302C of the first tool advancement device 302 prepares to advance the endovascular tool 102 through the patient lumen 104 (i.e., the advancement mechanism 302C of the first tool advancement device 302 and the advancement mechanism 304C of the second tool advancement device 304 may advance the endovascular tool 102 through the patient lumen 104 in sequence or one after the other).

In some embodiments, when the advancement mechanism 302C of the first tool advancement device 302 and/or the advancement mechanism 304C of the second tool advancement device 304 advance the endovascular tool 102 through the patient lumen 104, the first tool advancement device 302 and/or the second tool advancement device 304 may remain stationary on the rail systems 302B, 304B (i.e., not translate along the rail systems 302B, 304B).

In some embodiments, the first tool advancement device 302 may be configured to rotate the advancement mechanism 302C and/or the actuator 302A may be configured to rotate the advancement mechanism 302C. In some embodiments, the second tool advancement device 304 may be configured to rotate the advancement mechanism 304C and/or the actuator 304A may be configured to rotate the advancement mechanism 304C. The advancement mechanism 302C of the first tool advancement device 302 and/or the advancement mechanism 304C of the second tool advancement device 304 may be configured to rotate around an axis that may extend along a length of the endovascular tool 102. In some embodiments, the advancement mechanism 302C of the first tool advancement device 302 and/or the advancement mechanism 304C of the second tool advancement device 304 may be configured to rotate in order to rotate, roll, twist, and/or torque the endovascular tool 102.

The system of FIGS. 3A and 3B can be used with a catheter 103 and catheter device 252 as shown in FIG. 2C.

Figure 4A:
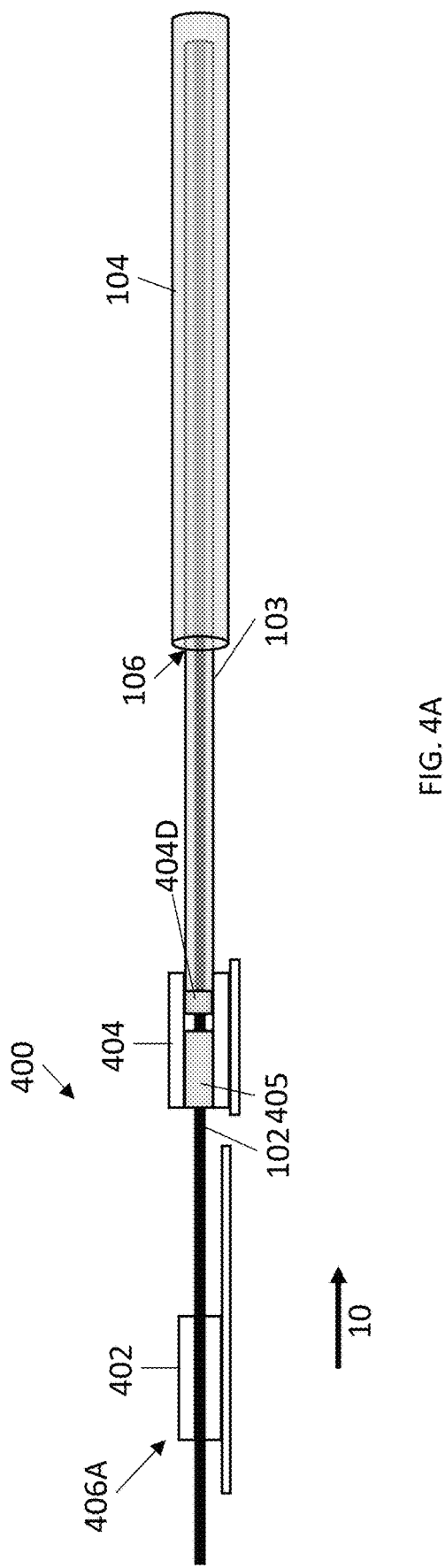
FIGS. 4A-4B illustrate another system for advancing a guidewire through a patient lumen according to some embodiments described herein.
Figure 4B:
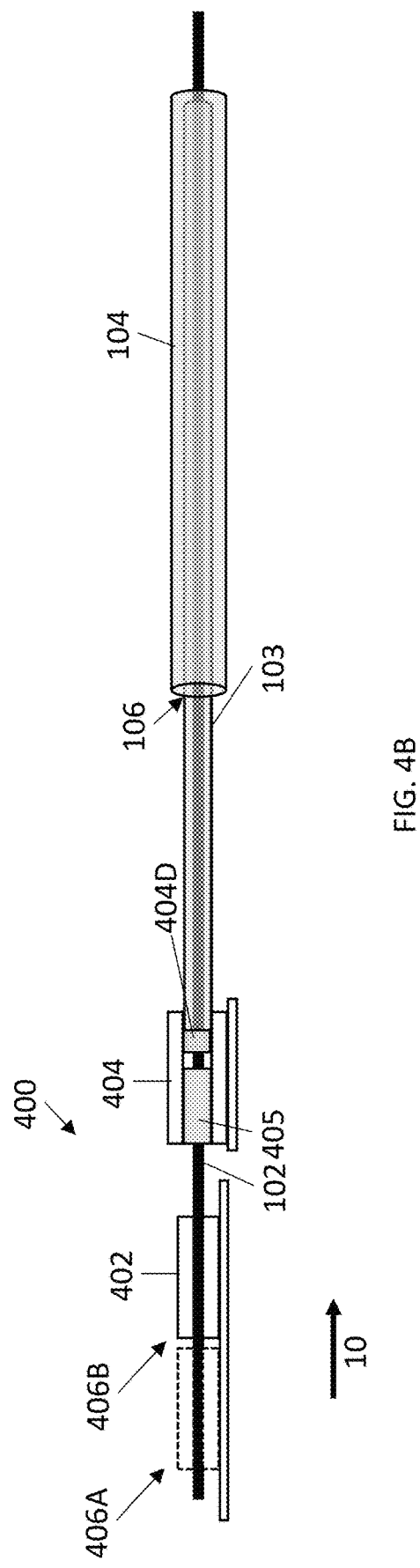

FIGS. 4A and 4B show a system 400 for advancing an endovascular tool 102 through a patient lumen. Common features between the systems 200, 300 and the system 400 will not be described again but are incorporated here in their entirety. The system 300 may include a first tool advancement device 402 and a second tool advancement device 404. In some embodiments, the second tool advancement device 404 may be coupled to a catheter 103. In some embodiments, the catheter 103 may include a Luer attachment mechanism 103A at a proximal end 103B of the catheter 103. In some embodiments, the second tool advancement device 404 may be coupled to the Luer attachment mechanism 103A of the catheter 103. In some embodiments, the second tool advancement device 404 may include a Luer mate 404D, and the second tool advancement device 404 may be coupled to catheter 103 and/or the Luer attachment mechanism 103A of the catheter 103 via the Luer mate 404D. In some embodiments, the catheter 103 and/or the Luer attachment mechanism 103A of the catheter may be screwed into or otherwise secured to the Luer mate 404D.

In some embodiments, the system 400 may include a torquer 405. The torquer 405 may be coupled to the endovascular tool 102 and/or the endovascular tool 102 may extend through the torquer 405. The torquer 405 may be positioned proximal to the catheter 103 and/or the Luer attachment mechanism 103A of the catheter 103.

In some embodiments, the second tool advancement device 404 may be coupled to the torquer 405 and/or the torquer 405 may be coupled to the second tool advancement device 404. In some embodiments, the second tool advancement device 404 may be configured to move (e.g., open and close) the torquer 405 between an open configuration and a closed configuration. In some embodiments, when the torquer 405 is in the open configuration, the torquer 405 may not contact or fixedly engage with the endovascular tool 102. Accordingly, the endovascular tool 102 may move relative to the torquer 405 so the endovascular tool 102 may advance through the torquer 405, the catheter 103, and/or a patient lumen 104. In some embodiments, when the torquer 405 is in the closed configuration, the torquer 405 may contact the endovascular tool 102. Accordingly, the torquer 405 may prevent the endovascular tool 102 from moving relative to the torquer 405 so the endovascular tool 102 may not advance through the torquer 405, the catheter 103, and/or the patient lumen 104.

In some embodiments, when the first tool advancement device 402 moves from a first position 406A to a second position 406B in order to advance the endovascular tool 102 through the patient lumen 104, the second tool advancement device 404 may move the torquer 405 to the open configuration so the endovascular tool 102 may advance through the patient lumen 104. In some embodiments, the second tool advancement device 404 may move the torquer 405 to the open configuration when the first tool advancement device 402 is positioned at the first position 406A. In some embodiments, the second tool advancement device 404 may move the torquer 405 to the open configuration before the first tool advancement device 402 moves from the first position 406A to the second position 406B.

In some embodiments, when the first tool advancement device 402 moves from the second position 406B to the first position 406A to prepare to advance the endovascular tool 102 through the patient lumen 104, the second tool advancement device may move the torquer 405 to the closed configuration in order to prevent or inhibit the first tool advancement device 402 from removing the endovascular tool 102 from the patient lumen 104. In some embodiments, the second tool advancement device 404 may move the torquer 405 to the closed configuration when the first tool advancement device 402 is positioned at the second position 406B. In some embodiments, the second tool advancement device 404 may move the torquer 405 to the closed configuration before the first tool advancement device 402 moves from the second position 406B to the first position 406A.

In some embodiments, a practitioner may control one or more functions, features, or components of the systems 200, 300, 400 via a computer system 1002, as described further below with reference to FIG. 13.

FIGS. 5A-5D show a first tool advancement device 502. In some embodiments, first tool advancement devices 202, 302, and 402 may include the first tool advancement device 502. In some embodiments, the first tool advancement device 502 may include a housing 510. In some embodiments, the housing 510 may include a top portion 510A and a bottom portion 510B. The top portion 510A may be removably coupled to the bottom portion 510B. In some embodiments, the housing 510 and/or the top portion 510A and the bottom portion 510B may include or define a recess 510C. The bottom portion 510B may be coupled to a rail system (not shown). The rail system may be configured to move the first tool advancement device 502 between a first position and a second position, as described above with reference to FIGS. 2A-2C and 4A-4B.

In some embodiments, as shown in FIG. 5B, the first tool advancement device 502 may include a first input 512 and a second input 514. In some embodiments, the first input 512 and/or the second input 514 may be remotely controlled via a computing system, a control system, and/or a controller. In some embodiments, the first input 512 and/or the second input 514 may be positioned between the top portion 510A of the housing 510 and the bottom portion 510B of the housing 510. In some embodiments, the top portion 510A may be uncoupled from the bottom portion 510B and the first input 512 and/or the second input 514 may be removed from the housing 510. In some embodiments, when the top portion 510A is coupled to the bottom portion 510B, the first input 512 and/or the second input 514 may rotate in a first direction (i.e., clockwise) and/or a second direction opposite the first direction (i.e., counterclockwise).

In some embodiments, as shown in FIG. 5C, the first input 512 may be configured interact with a first clamping device 516 and/or the second input 514 may be configured interact with a second clamping device 518. The first clamping device 516 may include a gear 516A and/or the second actuator 518 may include a gear 518A. In some embodiments, the gear 516A of the first clamping device 516 may interact with the first input 512 so that when the first input 512 is rotated, the first clamping device 516 may rotate. In some embodiments, the first input 512 may include a gear 512A configured to interact with the gear 516A of the first clamping device 516. In some embodiments, the gear 518A of the second clamping device 518 may interact with the second input 514 so that when the second input 514 is rotated, the second clamping device 518 may rotate. In some embodiments, the second input 514 may include a gear 514A configured to interact with the gear 518A of the second clamping device 518.

Figure 5A:
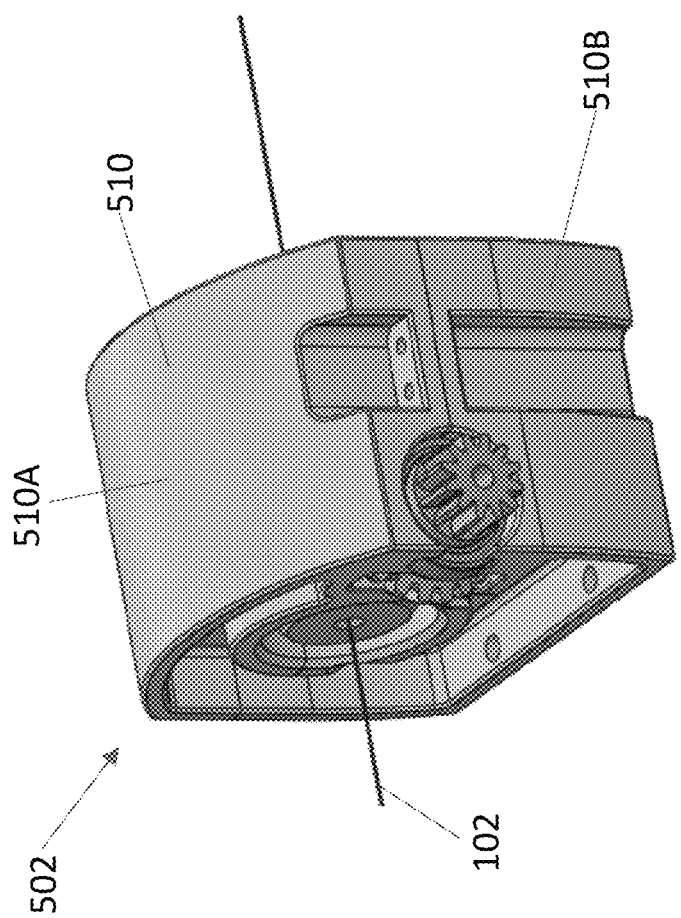
Figure 5D:
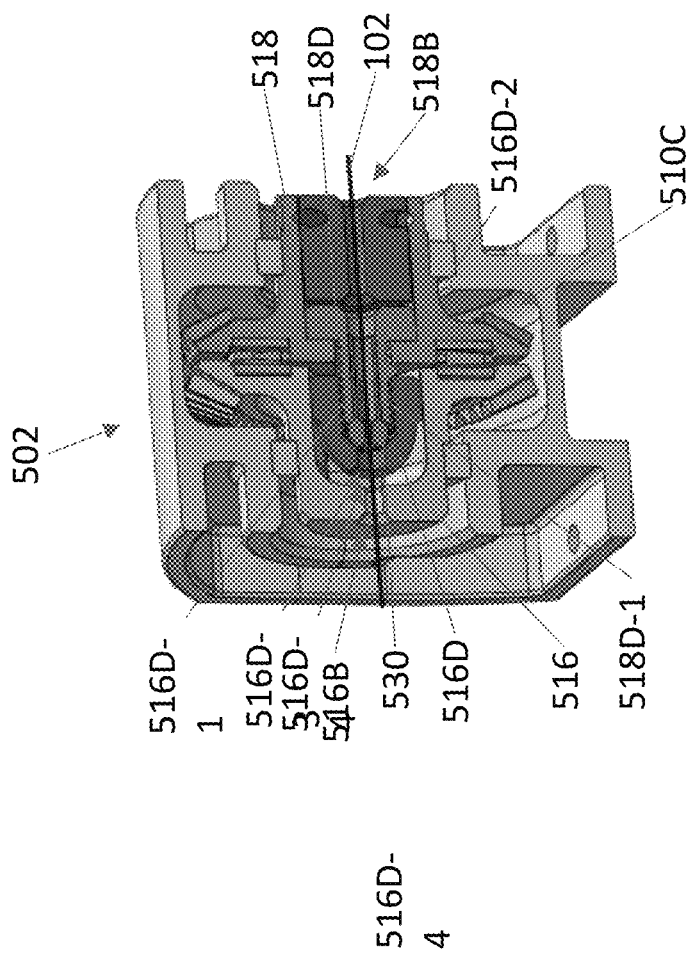
Figure 5E:
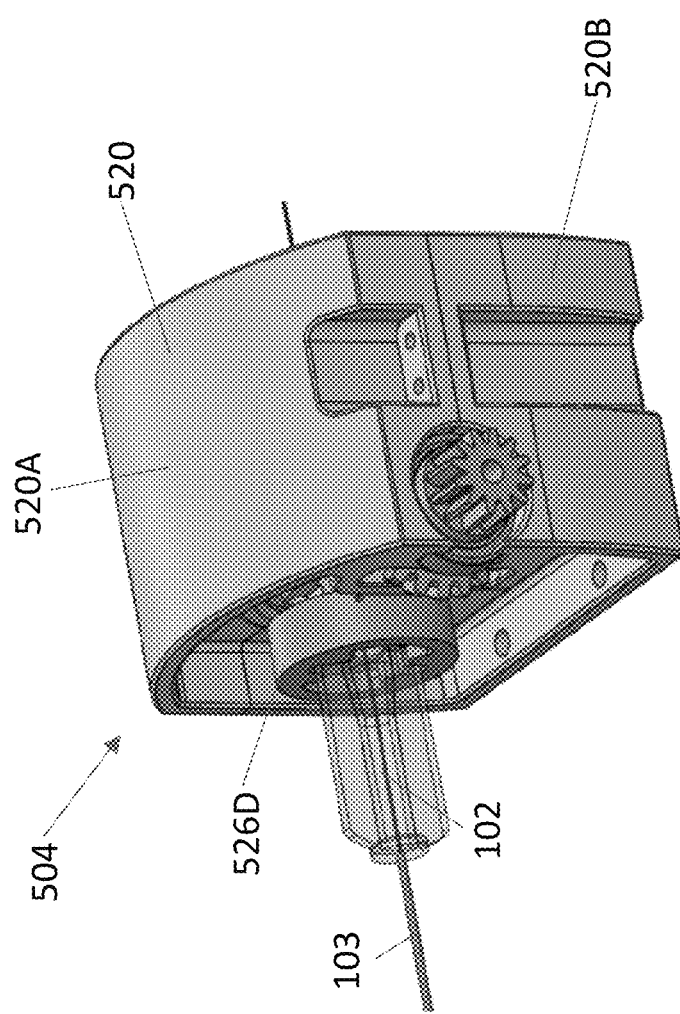

In some embodiments, as shown in FIG. 5D, the first clamping device 516 may include an opening 516B and/or the second clamping device 518 may include an opening 518B. In some embodiments, the opening 516B of the first clamping device 516 may be positioned at the center of the first clamping device 516 and/or the opening 518B of the second clamping device 518 may be positioned at the center of the second clamping device 518. In some embodiments, the endovascular tool 102 may be inserted through the opening 516B of the first clamping device 516 and/or the opening 518B of the second clamping device 518.

In some embodiments, the first clamping device 516 and/or the second clamping device 518 may be positioned in the recess 510C of the housing 510. In some embodiments, the first clamping device 516 and/or the second clamping device 518 may be rotatably coupled to or positioned in the housing 510 so the first clamping device 516 and/or the second clamping device 518 may rotate.

In some embodiments, the first clamping device 516 may be positioned distal to the second clamping device 518 so the first clamping device 516 is positioned closer to the patient lumen 104 than the second clamping device 518. In some embodiments, the second clamping device 518 may be positioned proximal to the first clamping device 516 so the second clamping device 518 is further from the patient lumen 104 than the first clamping device 516.

In some embodiments, the first clamping device 516 may include a recess 516C. The recess 516C may be configured to receive and/or hold a first collet clamp 516D. In some embodiments, the first collet clamp 516D may be configured to translate proximally and/or distally in the recess 516C. In some embodiments, the second clamping device 518 may include a recess 518C. The recess 518C may be configured to receive and/or hold a second collet clamp 518D. In some embodiments, the second collet clamp 518D may be configured to translate or move proximally and/or distally in the recess 518C. In some embodiments, the first collet clamp 516D may include a recess 516D-2 configured to receive the second collet clamp 518D. In some embodiments, the recess 516D-2 may include internal threading 516D-1 (i.e., female threading) and the second collet clamp 518D may include external threading 518D-1 (i.e., male threading).

In some embodiments, the first clamping device 516 and/or the second clamping device 518 may be positioned such that the second collet clamp 518D may extend from the recess 518C of the second clamping device 518 and into the first collet clamp 516D. In some embodiments, the external threading 518D-1 of the second collet clamp 518D may interact with the internal threading 516D-1 of the first collet clamp 516D to threadably couple the second collet clamp 518D to the first collet clamp 516D. In some embodiments, the second collet clamp 518D may translate towards (i.e., into the recess 516D-2) and/or away from (i.e., out of the recess 516D-2) the first collet clamp 516D when the second collet clamp 518D is rotated relative to the first collet clamp 516D.

In some embodiments, the first collet clamp 516D may be coupled to the first clamping device 516 so the first collet clamp 516D may rotate around the endovascular tool 102 when the first clamping device 516 rotates around the endovascular tool 102. In some embodiments, the second collet clamp 518D may be coupled to the second clamping device 518 so the second collet clamp 518D may rotate around the endovascular tool 102 when the second clamping device 518 rotates around the endovascular tool 102.

In some embodiments, the first clamping device 516 may be rotated relative to the second clamping device 518 and/or the second clamping device 518 may be rotated relative to the first clamping device 516. In some embodiments, the first clamping device 516 and the second clamping device 518 may rotate in opposite direction. In some embodiments, when the first clamping device 516 is rotated in a first direction and the second clamping device 518 is rotated in a second direction, the internal threading 516D-1 of the first collet clamp 516D and the external threading 518D-1 of the second collet clamp 518 may translate the second collet clamp 518 towards the first collet clamp 516D. In some embodiments, when the first clamping device 516 is rotated in the second direction and the second clamping device 518 is rotated in the first direction, the second collet clamp 518D may translate away from the first collet clamp 516D.

Figure 6:
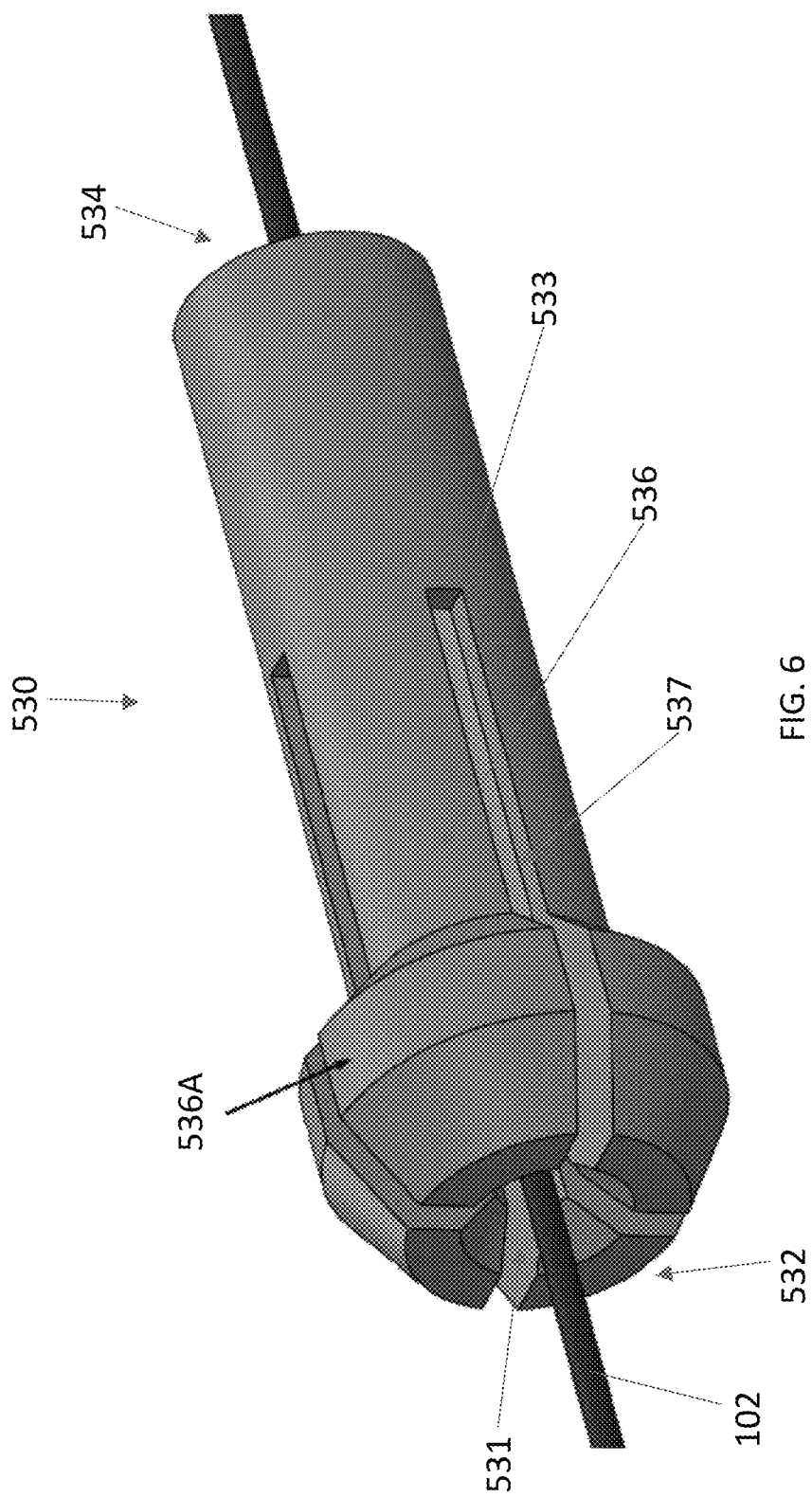
FIG. 6 illustrates a collet according to some embodiments described herein.

In some embodiments, the first tool advancement device 502 may include a collet 530, as shown in FIG. 6. In some embodiments, the collet 530 may be positioned in the second collet clamp 518D so the second collet clamp 518D and the collet 530 may be positioned concentrically around the endovascular tool 102.

In some embodiments, the collet 530 may include a cylindrical shape, a rectangular prism shape, and/or any other shape. The collet 530 may include distal end 532 and a proximal end 534. In some embodiments, the collet 530 may include an opening 531 extending through the collet 530 from the distal end 532 to the proximal end 534. In some embodiments, the endovascular tool 102 may be inserted into and/or through the collet 530 and/or the opening 531.

In some embodiments, the collet 530 may include clamps 536. In some embodiments, the clamps 536 may be positioned at the distal end 532 of the collet 530. In some embodiments, the clamps 536 may be spaced around the opening 531 and the clamps 536 may be separated by cutouts 537. The cutouts 537 may extend from an outer surface 533 of the collet 530 to the opening 531 and/or the cutouts 537 may extend from the distal end 532 to a position 535 between the distal end 532 and the proximal end 534. In some embodiments, the cutouts 537 may allow the clamps 536 to radially flex towards each other and/or away from each other.

In some embodiments, the clamps 536 may define the opening 531 at the distal end 532. In some embodiments, when the clamps 536 flex towards each other, the opening 531 at the distal end 532 may become smaller and/or the clamps 536 may contact the endovascular tool 102 inserted through the opening 531. Accordingly, when the clamps 536 contact the endovascular tool 102, the first tool advancement device 502 may be in the closed configuration, and the clamps 536 and/or the collet 530 may prevent or inhibit the endovascular tool 102 from translating through the opening 531 relative to the collet 530.

In some embodiments, a portion 536A of the clamps 536 positioned at the distal end 532 may extend radially outward from the collet 530. In some embodiments, as shown in FIG. 5C, when the second collet clamp 518D translates towards the first collet clamp 516D, the second collet clamp 518D may translate or move the collet 530 towards the first collet clamp 516D. In some embodiments, the first collet clamp 516D may include an opening 516D-3 at a distal end 516D-4 of the first collet clamp 516D. In some embodiments, the opening 516D-3 may be smaller than the recess 516D-2. Accordingly, when the collet 530 translates towards the first collet clamp 516D, the clamps 536 may flex towards each other in order to fit into the opening 516D-3 and/or the first collet clamp 516D may apply a force to the portion 536A of the clamps 536 so the clamps 536 may flex towards each other. In some embodiments, the second collet clamp 518D may apply a force to the portion 536A of the clamps 536 so the clamps 536 may flex towards each other. In some embodiments, the first collet clamp 516D and the second collet clamp 518D may apply a force to the portion 536A of the clamps 536.

In some embodiments, the first clamping device 516 and the second clamping device 518 may be rotated in the same direction around the endovascular tool 102. In some embodiments, the first clamping device 516 and the second clamping device 518 may both be rotated in the first direction or the first clamping device 516 and the second clamping device 518 may both be rotated in the second direction. In some embodiments, when the first clamping device 516 and the second clamping device 518 are rotated in the same direction, the first clamping device 516 may rotate the first collet clamp 516D and the second clamping device 518 may rotate the second collet clamp 518D. Accordingly, the first collet clamp 516D and the second collet clamp 518D may rotate around the endovascular tool 102 and the second collet clamp 518D may not translate towards or away from the first collet clamp 516D. In some embodiments, if the collet 530 is in the open configuration, the collet 530 may rotate around the endovascular tool 102. In some embodiments, if the collet 530 is in the closed configuration, the collet 530 may rotate, roll, twist, and/or torque the endovascular tool 102.

In some embodiments, the first input 512 may be positioned perpendicular or substantially perpendicular to the first clamping device 516. In some embodiments, as shown in FIG. 5C, the first input 512 may be positioned or configured to rotate around an axis 108 perpendicular to the endovascular tool 102 and/or the first clamping device 516 may be positioned or configured to rotate around the endovascular tool 102, as described above. In some embodiments, the second input 514 may be positioned perpendicular or substantially perpendicular to the second clamping device 518. In some embodiments, as shown in FIG. 5C, the second input 514 may be positioned or configured to rotate around the axis 108 perpendicular to the endovascular tool 102 and/or the second clamping device 518 may be positioned or configured to rotate around the endovascular tool 102, as described above.

FIGS. 5E-5H show a second tool advancement device 504. In some embodiments, the second tool advancement devices 204, 304, and 404 may include the second tool advancement device 504. In some embodiments, the second tool advancement device 504 may include a housing 520. In some embodiments, the housing 520 may include a top portion 520A and a bottom portion 520B. The top portion 520A may be removably coupled to the bottom portion 520B. In some embodiments, the housing 520 and/or the top portion 520A and the bottom portion 520B may include or define a recess 520C. The bottom portion 520B may be coupled to rail system (not shown). The rail system may be configured to move the second tool advancement device 504 between a third position and a fourth position, as described above with reference to FIGS. 2A-2C and 4A-4B.

Figure 5F:
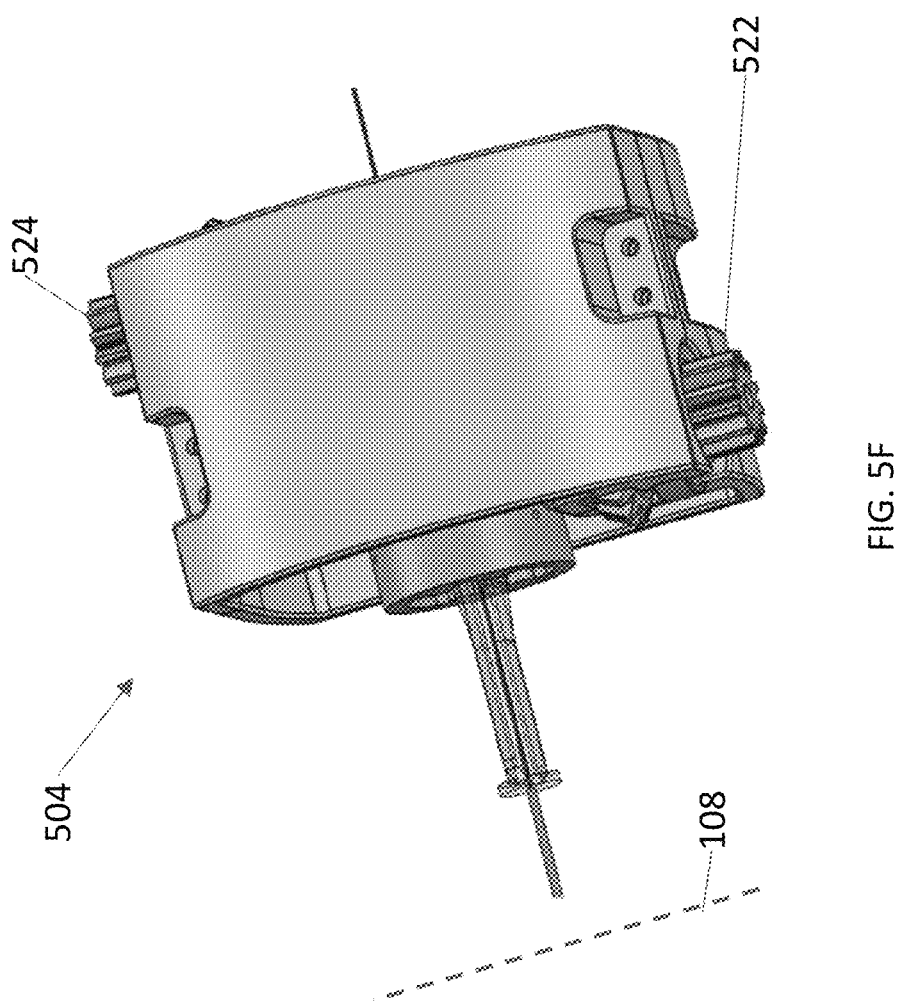

In some embodiments, as shown in FIG. 5F, the second tool advancement device 504 may include a first input 522 and a second input 524. In some embodiments, the first input 522 and/or the second input 522 may be remotely controlled via a computing system, a control system, and/or a controller. In some embodiments, the first input 522 and/or the second input 524 may be positioned between the top portion 520A of the housing 520 and the bottom portion 520B of the housing 520. In some embodiments, the top portion 520A may be uncoupled from the bottom portion 520B and the first input 522 and/or the second input 524 may be removed from the housing 510. In some embodiments, when the top portion 520A is coupled to the bottom portion 520B, the first input 522 and/or the second input 514 may rotate in a first direction (i.e., clockwise) and/or a second direction opposite the first direction (i.e., counterclockwise).

In some embodiments, as shown in FIG. 5G, the first input 522 may be configured to interact with a first clamping device 526 and/or the second input 524 may be configured to interact with a second clamping device 528. The first clamping device 526 may include a gear 526A and/or the second actuator 528 may include a gear 528A. In some embodiments, the gear 526A of the first clamping device 526 may interact with the first input 522 so that when the first input 522 is rotated, the first clamping device 526 may rotate. In some embodiments, the first input 522 may include a gear 522A configured to interact with the gear 526A of the first clamping device 526. In some embodiments, the gear 528A of the second clamping device 528 may interact with the second input 524 so that when the second input is rotated 524, the second clamping device 528 may rotate. In some embodiments, the second input 524 may include a gear 524A configured to interact with the gear 528A of the second clamping device 528.

Figure 5H:
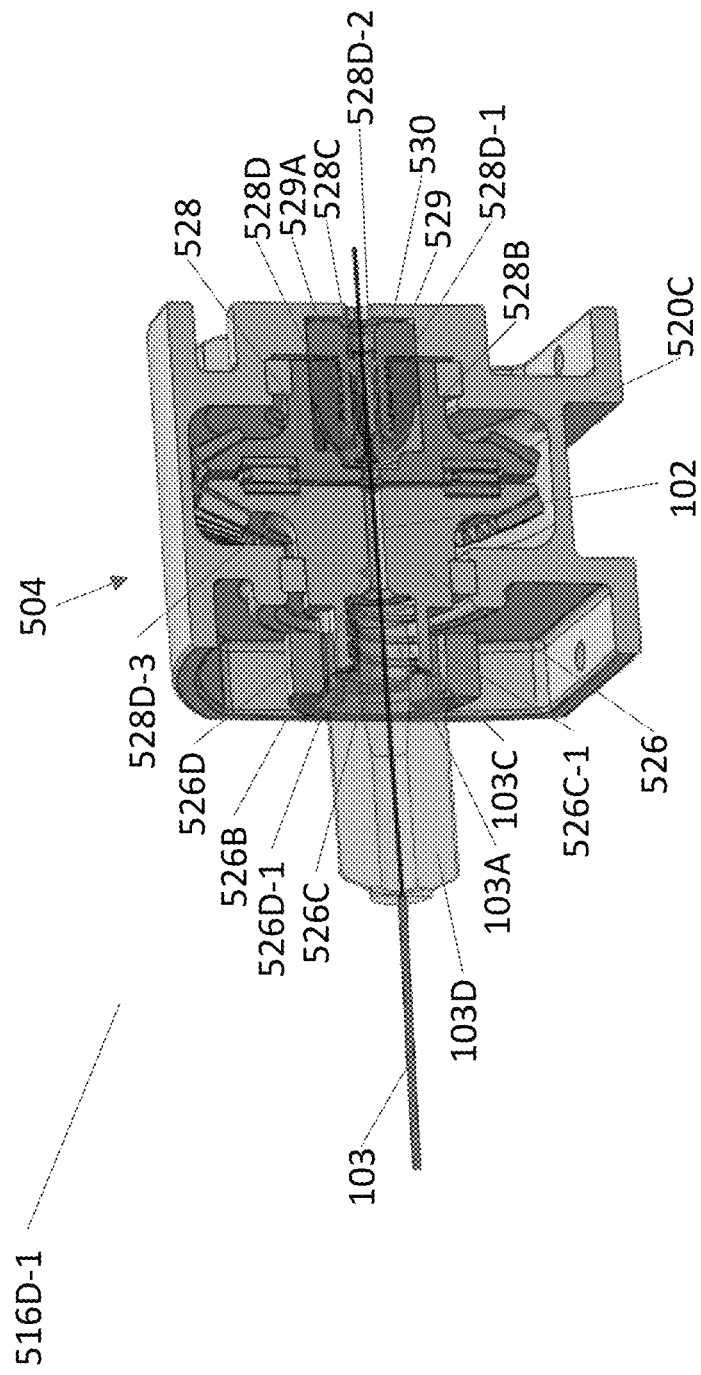

In some embodiments, as shown in FIG. 5H, the first clamping device 526 may include an opening 526B and/or the second clamping device 528 may include an opening 528B. In some embodiments, the opening 526B of the first clamping device 526 may be positioned at the center of the first clamping device 526 and/or the opening 528B may of the second clamping device 528 may be positioned at the center of the second clamping device 528. In some embodiments, the endovascular tool 102 may be inserted through the opening 526B of the first clamping device 526 and/or the opening 528B of the second clamping device 528.

In some embodiments, the first clamping device 526 and/or the second clamping device 528 may be positioned in the recess 520C of the housing 520. In some embodiments, the first clamping device 526 and/or the second clamping device 528 may be rotatably coupled to or positioned in the housing 520 so the first clamping device 526 and/or the second clamping device 528 may rotate.

In some embodiments, the first clamping device 526 may be positioned distal to the second clamping device 528 so the first clamping device 526 is positioned closer to the patient lumen than the second clamping device 528. In some embodiments, the second clamping device 528 may be positioned proximal to the first clamping device 526 so the second clamping device 528 is further from the patient lumen 104 than the first clamping device 526.

In some embodiments, the first clamping device 526 may include a recess 526C. In some embodiments, the first clamping device 526 and/or the recess 526C may be configured to extend distally from the housing 520. The recess 526C may be configured to receive the microcatheter 103 and/or the Luer attachment mechanism 103A of the microcatheter 103. In some embodiments, the microcatheter 103 and/or the Luer attachment mechanism 103A may be coupled to the first clamping device 526 and/or the recess 526C. In some embodiments, the endovascular tool 102 may be inserted through the microcatheter 103 when the microcatheter 103 and/or the Luer attachment mechanism 103A are coupled to the first clamping device 526 and/or the recess 526C In some embodiments, the recess 526C may include internal threading 526C-1 (i.e., female threading). In some embodiments, the internal threading 526C-1 may be configured to interact with external threading 103C (i.e., male threading) of the Luer attachment mechanism 103A. In some embodiments, the internal threading 526C-1 and/or the external threading 103C may couple the Luer attachment mechanism 103A and/or the microcatheter 103 to the recess 526C and/or the first clamping device 526.

In some embodiments, the first clamping device 526 may include a microcatheter securement device 526D. In some embodiments, the microcatheter securement device 526D may include a ring shape. In some embodiments, the microcatheter securement device 526D may include one or more indentations 526D-1. In some embodiments, the microcatheter securement device 526D may be slidably coupled to the first clamping device 526. In some embodiments, the microcatheter securement device 526D may be coupled to the first clamping device 526 when the microcatheter 103 is coupled to the first clamping device 526. In some embodiments, the microcatheter securement device 526D may be inserted onto the first clamping device 526. In some embodiments, the one or more indentations 526D-1 may be positioned so the one or more indentations 526D-1 are inserted over flanges 103D of the microcatheter 103.

In some embodiments, when the first clamping device 526 rotates in a first direction, the first clamping device 526 may rotate the microcatheter 103 in the first direction and/or when the first clamping device 526 rotates in a second direction, the first clamping device 526 may rotate the microcatheter 103 in the second direction. In some embodiments, when the first clamping device 526 rotates the first clamping device 526 may rotate the microcatheter securement device 526D. In some embodiments, the microcatheter securement device 526D may apply a rotational force to a portion of the flanges 103D in the one or more indentations 526D-1 to rotate the flanges 103D and/or the microcatheter 103.

In some embodiments, the second clamping device 528 may include a recess 528C. In some embodiments, the recess 528C may be configured to receive and/or hold a first collet clamp 528D. In some embodiments, the first collet clamp 528D may include a recess 528D-2 with internal threading 528D-1. In some embodiments, the recess 528D-2 of the first collet clamp 528D may be configured to receive a second collet clamp 529. In some embodiments, the second collet clamp 529 may include external threading 529A. In some embodiments, the second collet clamp 529 may be positioned in the recess 520C of the housing 520. In some embodiments, the second collet clamp 529 may be coupled to or fixed to the housing 510. In some embodiments, the second collet clamp 529 may be positioned proximal to the first clamping device 526 and the second clamping device 528.

In some embodiments, the second collet clamp 529 may be positioned so the second collet clamp 529 may extend into the recess 528C of the second clamping device 528 and/or the first collet clamp 528D. In some embodiments, the external threading 529A of the second collet clamp 529 may interact with the internal threading 528D-1 of the first collet clamp 528D to threadably couple the second collet clamp 529 to the first collet clamp 528D. In some embodiments, when the first collet clamp 528D rotates in a first direction, the first collet clamp 528D may translate towards the second collet clamp 529 (i.e., the second collet clamp 529 may translate into the recess 528D-2).

In some embodiments, the second tool advancement device 504 may include a collet 530, as described above with reference to FIG. 6. In some embodiments, the collet 530 may be positioned in the second collet clamp 529 so the second collet clamp 529 and the collet 530 may be positioned concentrically around the endovascular tool 102. In some embodiments, the second clamping device 528 may be rotated around the endovascular tool 102. In some embodiments, when the second clamping device 528 is rotated in a first direction, the first collet clamp 528D may rotate relative to the second collet clamp 529 in the first direction. Accordingly, the internal threading 528D-1 of the first collet clamp 528D and the external threading 529A of the second collet clamp 529 may translate the first collet clamp 528D towards the second collet clamp 529. When the first collet clamp 528D translates towards the second collet clamp 529, the first collet clamp 528D may translate toward the collet 530. In some embodiments, the first collet clamp 528D may include an opening 528D-3 at a distal end 528D-4 of the first collet clamp 528D. In some embodiments, the opening 528D-3 may be smaller than the recess 528D-2. Accordingly, when the first collet clamp 528D translates towards the collet 530, the clamps 536 of the collet 530 may flex towards each other in order to fit into the opening 528D-2 and/or the first collet clamp 528D may apply a force to the portion 536A of the clamps 536 so the clamps 536 may flex towards each other. In some embodiments, the second collet clamp 529 may apply a force to the portion 536A of the clamps 536 so the clamps 536 may flex towards each other (i.e., the closed configuration) so the clamps 56 contact the endovascular tool 102. In some embodiments, the first collet clamp 5528D and the second collet clamp 529 may apply a force to the portion 536A of the clamps 536.

In some embodiments, when the second clamping device 528 is rotated in a second direction opposite the first direction, the first collet clamp 528D may rotate relative to the second collet clamp 529 in the second direction. Accordingly, the internal threading 528D-1 of the first collet clamp 528D and the external threading 529A of the second collet clamp 529 may translate the first collet clamp 528D away from the second collet clamp 529. When the first collet clamp 528D translates away from the second collet clamp 529, the first collet clamp 528D may translate away from the collet 530. Accordingly, the first collet clamp 528D and/or the second collet clamp 529 may apply a smaller force or no force to the portion 536A of the clamps 536, and the clamps 536 may flex away from each other (i.e., the open configuration) so the clamps 536 do not contact the endovascular tool 102.

In some embodiments, the first input 522 may be positioned perpendicular or substantially perpendicular to the first clamping device 526. In some embodiments, FIG. 5G, the first input device may be positioned or configured to rotate around the axis 108 perpendicular to the endovascular tool 102 and/or the first clamping device 526. In some embodiments, the second input 524 may be positioned perpendicular or substantially perpendicular to the second clamping device 528. In some embodiments, as shown in FIG. 5G, the second input 524 may be positioned or configured to rotate around the axis 108 perpendicular to the endovascular tool 102 and/or the second clamping device 528 may be positioned or configured to rotate around the endovascular tool 102, as described above.

The systems described above advance or retract the elongate tool or endovascular tool 102 using discrete motion of two tool advancement devices (e.g., tool advancement devices 202, 204) which each alternately fixedly engage with the elongate tool and advance or retract the tool a short linear distance and then release the elongate tool and reset to a starting position. The motions of the tool advancement devices, referred to below by their relative positions as the proximal device or proximal elongate tool device (the device located away from the patient) and the distal device or distal elongate tool device (the device located towards the patient) can be coordinated to provide smooth, continuous, and/or uninterrupted insertion and retraction. That is, with coordinated motion of the proximal and distal devices, the elongate tool can be inserted and retracted in a smooth, continuous, and/or uninterrupted manner for a distance that is greater than a stroke length of either of the proximal and distal devices. Providing smooth, continuous, and/or uninterrupted insertion and/or retraction is advantageous as this type of motion is expected by an operator of a robotic surgical system controlling the system.

Figure 7:
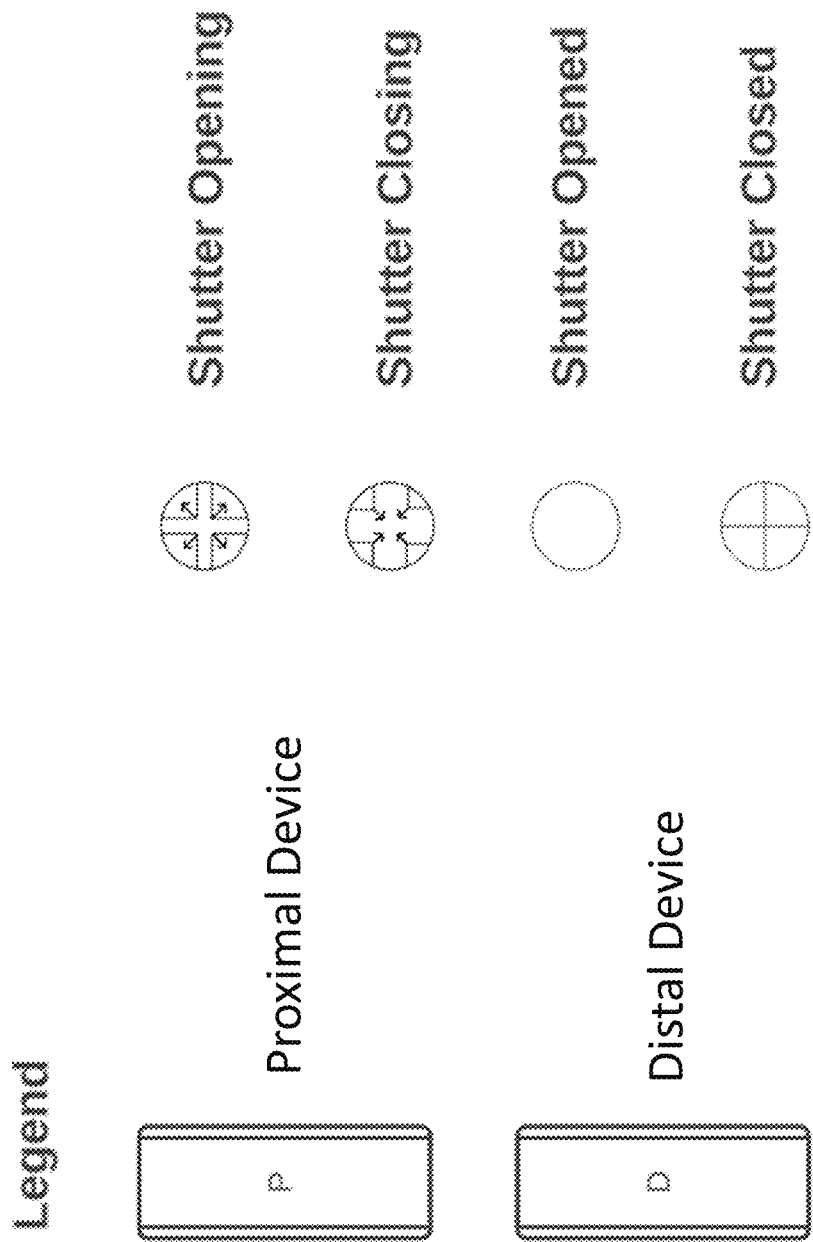
FIG. 7 is a legend illustrating symbols used in FIGS. 8-11.

Smooth, continuous, and/or uninterrupted insertion and retraction of an elongate body can be achieved by sequentially transitioning the proximal device and the distal device through a plurality of different states to achieve a coordinated motion. FIG. 7 provides a legend illustrating various symbols that are used in FIGS. 8-11. FIG. 8 illustrates various sequential states for the proximal device and a distal device to insert the elongate tool in a smooth, continuous, and/or uninterrupted manner. FIG. 9 illustrates various sequential states for the proximal device and the distal device to retract the elongate tool in a smooth, continuous, and/or uninterrupted manner.

With reference first to FIG. 7, the proximal device can be, for example, any of the first tool advancement devices described above. In general, the proximal device can be configured to move linearly in proximal and distal directions. In some embodiments, the proximal device is configured to remain stationary, and a portion of the proximal device is configured to move linearly in the proximal and distal directions. The proximal device also includes a proximal shutter or clamp that is configured to transition between an open state and a closed state. In the open state, the proximal shutter allows or permits an elongate tool to move freely through the proximal shutter. In the closed state, the elongate tool is fixedly held by the proximal shutter. In the closed state, when the proximal device moves proximally or distally, the elongate body is moved proximally or distally with the proximal device. One detailed non-limiting example of a proximal device is shown in FIGS. 5A-5D, although other embodiments are certainly possible.

The distal device can be for example, any of the second tool advancement devices described above. In general, the distal device can be configured to move linearly in proximal and distal directions. In some embodiments, the distal device is configured to remain stationary, and a portion of the distal device is configured to move linearly in the proximal and distal directions. The distal device also includes a distal shutter or clamp that is configured to transition between an open state and a closed state. In the open state, the distal shutter allows or permits the elongate tool to move freely through the distal shutter. In the closed state, the elongate tool is fixedly held by the distal shutter. In the closed state, when the distal device moves proximally or distally, the elongate body is moved proximally or distally with the distal device. One detailed non-limiting example of a distal device is shown in FIGS. 5E-5H, although other embodiments are certainly possible.

FIG. 7 includes symbols representing the proximal device, the distal device, as well as the state of the shutter of the proximal device and distal device. For example, the shutter can be either opening, closing, opened, or closed.

A system (such as shown, for example, in FIG. 13) or other computer or robotic system can include at least one processor and at least one electronic storage medium, the at least electronic storage medium storing instructions configured to cause the at least one processor to coordinate motion of the proximal device and the distal device to continuously advance the elongate tool in the distal direction in a smooth, continuous, and/or uninterrupted manner. As shown in FIG. 8, for example, this can be achieved by transitioning the distal device and the proximal device sequentially through one or more of the illustrated states. Notably, insertion can begin at any state and will move sequentially forward through the states with the eighth state being followed by the first state.

As shown in FIG. 8, in the first state, the proximal device is moving in the distal direction and the proximal shutter is closed. The distal device is moving in the distal direction and the distal shutter is closing. Because the proximal shutter is closed, the proximal shutter is fixedly engaged with the proximal device and the elongate tool is carried in the distal direction along with the movement of the proximal device. The distal device is moving distally as well as the distal shutter is closing. Because the shutter is closed, it does not yet fixedly engage the elongate tool. Still, the distal device moves distally to provide a smooth handoff between the proximal device and the distal device. For example, the distal device can move distally to match the velocity of the distal device. In FIG. 8, the states represent transitions between different configurations or configurations themselves as shown in FIG. 12. The first state corresponds to a transition from the sixth configuration to the fifth configuration (see FIG. 12).

In the second state, the proximal device is moving in the distal direction and the proximal shutter is opening. The distal device is moving in the distal direction and the distal shutter is closed. This state represents a handoff of the elongate tool from the proximal device to the distal device. As the proximal device and the distal device move distally, for example, at the same velocity, the shutter of the proximal device opens (releasing the elongate tool) as the shutter of the distal device is closed (fixedly engaged with the elongate tool). The second state represents a transition from the fifth configuration to the fourth configuration (see FIG. 12). The handoff between the proximal and distal device occurs smoothly and the movement of the elongate tool remains smooth, continuous, and/or uninterrupted.

In the third state, the proximal device is moving in the proximal direction and the proximal shutter is open. The distal device is moving in the distal direction and the distal shutter is closed. The shutter of the proximal device is open such that the proximal device is not engaged with the elongate tool. This allows the proximal device to move freely without affecting the motion of the elongate tool. In the third state, the proximal device moves proximally to reset its position so that it will be able to take another stroke. At the same time, the shutter of the distal device is closed, and the distal device is fixedly engaged with the elongate tool. As the distal device moves in the distal direction, the elongate body is carried distally with the movement of the distal device. The third state represents a transition from the fourth configuration to the third configuration (see FIG. 12).

In the fourth state, the proximal device is moving in the distal direction and the proximal shutter is open. The distal device is moving in the distal direction and the distal shutter is closed. In this state, the shutter of the distal device is still closed, and the distal device is still fixedly engaged with the elongate tool. As the distal device moves in the distal direction, the elongate body is still carried distally with the movement of the distal device. At the same time, the proximal device moves in the distal direction with its shutter open and disengaged from the elongate body to, for example, match the velocity of the distal device. This state represents the third configuration of FIG. 12.

In the fifth state, the proximal device is moving in the distal direction and the proximal shutter is closing. The distal device is moving in the distal direction and the distal shutter is closed. The distal device remains fixedly engaged with the elongate tool, which is carried in the distal direction with movement of the distal device. The proximal device is closing its shutter in preparation to engage the elongate tool while moving distally to, for example, match the velocity of the distal device. The fifth state represents a transition from the third configuration to the second configuration (see FIG. 12).

In the sixth state, the proximal device is moving in the distal direction and the proximal shutter is closed. The distal device is moving in the distal direction and the distal shutter is opening. This state represents a handoff of the elongate tool from the distal device to the proximal device. As the distal device and the proximal device move distally, for example, at the same velocity, the shutter of the distal device opens (releasing the elongate tool) as the shutter of the proximal device is closed (fixedly engaged with the elongate tool). The sixth state represents a transition from the second configuration to the first configuration (see FIG. 12). The handoff between the distal and proximal device occurs smoothly and the movement of the elongate tool remains smooth, continuous, and/or uninterrupted.

In the seventh state, the proximal device is moving in the distal direction and the proximal shutter is closed. The distal device is moving in the proximal direction and the distal shutter is open. Because the shutter of the proximal device is closed, the proximal device is fixedly engaged with the elongate tool and the elongate tool is carried in the distal direction with the distal movement of the proximal device. In the third state, the distal device moves proximally to reset its position so that it will be able to take another stroke. The shutter of the distal device is open so that this proximal movement does not affect the distal movement of the elongate tool as it is carried by the proximal device. The seventh state represents the transition from the first configuration to the sixth configuration (see FIG. 12).

In the eighth state, the proximal device is moving in the distal direction and the proximal shutter is closed. The distal device is moving the distal direction, and the distal shutter is open. The proximal device carries the elongate body distally with its movement because its shutter is fixedly engaged with the elongate tool. The distal device moves distally to, for example, match the velocity of the proximal device in preparation for handoff.

After the eighth state, this cycle can return to the first state for continued insertion.

The system can also be configured coordinate motion of the proximal device and the distal device to continuously retract the elongate tool in the proximal direction in a smooth, continuous, and/or uninterrupted manner. As shown in FIG. 9, for example, this can be achieved by transitioning the distal device and the proximal device sequentially through one or more of the illustrated states. Notably, retraction can begin at any state and will move sequentially forward through the states with the eighth state being followed by the first state.

In the first state, the proximal device is moving in the proximal direction and the proximal shutter is closing. The distal device is moving in the proximal direction and the distal shutter is closed. Because the shutter of the distal device is closed, the distal device is fixedly engaged with the elongate tool and the elongate tool is carried in the proximal direction with the proximal movement of the distal device. At the same time, the proximal device moves in the proximal direction, for example, to match the speed of the distal device as its shutter is closing to provide a smooth handoff from the distal device to the proximal device. The first state represents a transition from the fourth configuration to the fifth configuration of FIG. 12.

In the second state, the proximal device is moving in the proximal direction and the proximal shutter is closed. The distal device is moving in the proximal direction and the distal shutter is opening. The shutter of the proximal device is now closed such that the proximal device is now engaged with the elongate body. The elongate body is therefore now carried in the proximal direction with the proximal movement of the proximal device. At the same time, the distal device is opening its shutter to release the elongate body handing off the elongate body from the distal device to the proximal device. The distal device and the proximal device can be moving at the same velocity such that the handoff from the distal device to the proximal device results in smooth, continuous, and/or uninterrupted motion of the elongate body in the proximal direction. The second state represents a transition from the fifth configuration to the sixth configuration (see FIG. 12).

In the third state, the proximal device is moving in the proximal direction and the proximal shutter is closed. The distal device is moving in the distal direction and the distal shutter is open. With the shutter of the proximal device closed, the proximal device is fixedly engaged with the elongate body and the elongate body is moved in the proximal direction with the proximal movement of the proximal device. At the same time, the distal device is disengaged from the elongate body with its shutter open, allowing it to move distally to reset for another stroke. The third state represents a transition from the sixth configuration to the first configuration (see FIG. 12).

In the fourth state, the proximal device is moving in the proximal direction and the proximal shutter is closed. The distal device is moving in the proximal direction and the distal shutter is open. With the shutter of the proximal device closed, the proximal device is fixedly engaged with the elongate body and the elongate body is moved in the proximal direction with the proximal movement of the proximal device. At the same time, the distal device moves in the proximal direction, for example, to match the speed of the proximal device as its shutter is closing to provide a smooth handoff from the proximal device to the distal device. The fourth state represents the first configuration of FIG. 12.

In the fifth state, the proximal device is moving in the proximal direction and the proximal shutter is closed. The distal device is moving in the proximal direction and the distal shutter is closing. With the shutter of the proximal device closed, the proximal device is fixedly engaged with the elongate body and the elongate body is moved in the proximal direction with the proximal movement of the proximal device. The distal device moves proximally to, for example, match the velocity of the proximal device as its shutter closes. The fifth state represents a transition from the first configuration to the second configuration (see FIG. 12).

In the sixth state, the proximal device is moving in the proximal direction and the proximal shutter is opening. The distal device is moving in the proximal direction and the distal shutter is closed. With the shutter of the distal device closed, the distal device is fixedly engaged with the elongate body and the elongate body is moved in the proximal direction with the proximal movement of the distal device. The shutter of the proximal device opens while the proximal device is moving proximally to provide smooth handoff from the proximal device to the distal device. The sixth state presents a transition from the second configuration to the third configuration (see FIG. 12).

In the seventh state, the proximal device is moving in the distal direction and the proximal shutter is open. The distal device is moving in the proximal direction and the distal shutter is closed. With the shutter of the distal device closed, the distal device is fixedly engaged with the elongate body and the elongate body is moved in the proximal direction with the proximal movement of the distal device. At the same time, the proximal device is disengaged from the elongate body with its shutter open, allowing it to move distally to reset for another stroke. The seventh state represents a transition from the third configuration to the fourth configuration (see FIG. 12).

In the eighth state, the proximal device is moving in the proximal direction and the proximal shutter is closing. The distal device is moving in the proximal direction and the distal shutter is closed. With the shutter of the distal device closed, the distal device is fixedly engaged with the elongate body and the elongate body is moved in the proximal direction with the proximal movement of the distal device. At the same time, the proximal device moves proximally to, for example, match the velocity of the distal device in preparation for the handoff of the elongate tool. The eighth state represents the fourth configuration of FIG. 12.

After the eighth state, this cycle can return to the first state for continued retraction.

Using the states of FIGS. 8 and 9, the system can provide for smooth, continuous, and/or uninterrupted insertion or retraction. The system can also be configured to transition between insertion and retraction by moving backwards and forwards through the configurations of FIG. 12. For example, as shown in FIG. 8, insertion involves moving backwards through the configuration, and as shown in FIG. 9, retraction involves moving forwards through the configurations. From any configuration, the elongate tool can be moved in the opposite direction by finding the corresponding state to transition from the current configuration to the previous configuration (for insertion) or the next configuration (for retraction).

As described above with reference to FIG. 2C, in some embodiments, a system can be configured to use an elongate tool, such as a guidewire, a coil, a stent, a flow diverter, or a stent retriever, in connection with a catheter (such as a microcatheter, a steerable catheter, or other elongate body having a lumen formed therethrough). The catheter can be coupled to a catheter device. For example, the catheter device can be configured to fixedly engage with the catheter. The catheter device (or a portion thereof) can be configured to move linearly in proximal and distal directions. The motion of the catheter device can cause linear insertion and/or retraction of the catheter. In some embodiments, the catheter device can remain stationary and include a feeder mechanism (e.g., one or more rollers) that engage with the catheter and drive insertion or retraction thereof.

The elongate body can be inserted and retracted as well using proximal and distal devices (now referred to as a distal elongate tool device and a proximal elongate tool device). The elongate body extends from the lumen of the catheter through the shutters of the proximal elongate tool device and the distal elongate tool device. The distal elongate tool device can be positioned proximal to the catheter device and can be configured to move linearly in the proximal and distal directions. The distal elongate tool device can include a distal clamp or shutter, wherein the elongate tool extends from the lumen of the catheter through the distal clamp, and wherein the distal clamp is configured to transition between an open state in which the elongate tool moves freely through the distal clamp and a closed state in which the elongate tool is fixedly held by the distal clamp. The proximal elongate tool device can be positioned proximal to the distal elongate tool device and can be configured to move linearly in the proximal and distal directions. The distal elongate tool device can include a proximal clamp or shutter, wherein the elongate tool extends from the distal clamp through the proximal clamp, and wherein the proximal clamp is configured to transition between an open state in which the elongate tool moves freely through the proximal clamp and a closed state in which the elongate tool is fixedly held by the proximal clamp.

In some instances, it may be desirable to park the elongate tool (e.g., not advance or retract the tool), while the catheter is moved (inserted or retracted) over elongate tool. When this happens the distances between the catheter device and the distal and proximal elongate tool devices can change. It can be advantageous to maintain a desired relationship between these devices. For example, as the distance between the catheter device and the distal elongate tool device increases, the elongate tool may be prone to buckling. Thus, it may be desirable to readjust positions of the distal elongate tool device and the proximal elongate tool device while maintaining the elongate tool parked. This may also advantageously keep the distal elongate tool device and the proximal elongate tool device in a position from which insertion or retraction of the elongate tool is immediately achievable, which is desirable.

FIG. 10 illustrates various sequential states for a catheter device, a proximal elongate tool device, and a distal elongate tool device to insert a catheter while parking the elongate tool device. Notably, during each state, the catheter device is inserting the catheter in a distal direction. For example, the catheter device is moving in a distal direction to cause insertion of the catheter in the distal direction.

In the first state, the proximal elongate tool device is not moving, and the proximal shutter is closed. The distal elongate tool device is not moving and the distal shutter is opening. With the shutter of the proximal elongate tool device closed, the proximal elongate tool device maintains the position of the elongate tool (e.g., keeps the elongate tool parked). At the same time, the shutter of the distal elongate tool device is opening, releasing the elongate tool in preparation for movement of the distal elongate tool device. This is representative of the transition from the fifth to the sixth configuration (see FIG. 12).

In the second state, the proximal elongate tool device is not moving, and the proximal shutter is closed. The distal elongate tool device is moving in the distal direction and the distal shutter is open. With the shutter of the proximal elongate tool device closed, the proximal elongate tool device maintains the position of the elongate tool (e.g., keeps the elongate tool parked). With the shutter of the distal elongate tool device open, the distal elongate tool device moves distally without affecting the position of the elongate tool, which remains parked. This distal motion moves the distal elongate tool device closer into proximity with the catheter device. This is representative of the transition from the sixth to the first configuration (see FIG. 12).

In the third state, the proximal elongate tool device is not moving, and the proximal shutter is closed. The distal elongate tool device is not moving and the distal shutter is open. With the shutter of the proximal elongate tool device closed, the proximal elongate tool device maintains the position of the elongate tool (e.g., keeps the elongate tool parked). At this stage, the distal elongate tool device has moved into a closer proximity to the catheter device and stopped moving. This represents the first configuration in FIG. 12.

In the fourth state, the proximal elongate tool device is not moving, and the proximal shutter is closed. The distal elongate tool device is not moving and the distal shutter is closing. With the shutter of the proximal elongate tool device closed, the proximal elongate tool device maintains the position of the elongate tool (e.g., keeps the elongate tool parked). The shutter of the distal elongate tool device is now closing. This represents the transition from the first to the second configuration (see FIG. 12).

In the fifth state, the proximal elongate tool device is not moving, and the proximal shutter is opening. The distal elongate tool device is not moving and the distal shutter is closed. The shutter of the distal elongate tool device is now closed. With the shutter of the distal elongate tool device closed, the distal elongate tool device maintains the position of the elongate tool (e.g., keeps the elongate tool parked). The shutter of the proximal elongate tool device is now opening, releasing the elongate tool. This represents the transition from the second to the third configuration (see FIG. 12).

In the sixth state, the proximal elongate tool device is moving in the distal direction and the proximal shutter is open. The distal elongate tool device is not moving, and the distal shutter is closed. With the shutter of the distal elongate tool device closed, the distal elongate tool device maintains the position of the elongate tool (e.g., keeps the elongate tool parked). With the shutter of the proximal elongate tool device open, the proximal elongate tool device moves distally without affecting the position of the elongate tool, which remains parked. This distal motion moves the proximal elongate tool device closer into proximity with the distal elongate tool device. This is representative of the transition from the third to the fourth configuration (see FIG. 12).

In the seventh state, the proximal elongate tool device is not moving, and the proximal shutter is open, and the distal elongate tool device is not moving and the distal shutter is closed. With the shutter of the distal elongate tool device closed, the distal elongate tool device maintains the position of the elongate tool (e.g., keeps the elongate tool parked). The proximal elongate tool device is now located in proximity to the distal elongate tool device. This represents the fourth configuration in FIG. 12.

In the eighth state, the proximal elongate tool device is not moving, and the proximal shutter is closed. The distal elongate tool device is not moving and the distal shutter is opening. With the shutter of the distal elongate tool device closed, the distal elongate tool device maintains the position of the elongate tool (e.g., keeps the elongate tool parked). The shutter of the proximal elongate tool is now closing in preparation for a handoff of the elongate tool. This represents a transition from the fourth to the fifth configuration (see FIG. 12). Notably, the catheter device has moved away from the distal elongate tool device.

After the eighth state, this cycle can return to the first state. By sequentially moving through these states, the distal elongate tool device and the proximal elongate tool device walk along the parked elongate tool in the distal direction to maintain a desired position relative to the catheter device as the catheter device moves in the distal direction.

FIG. 11 illustrates various sequential states for a catheter device, a proximal elongate tool device, and a distal elongate tool device to retract a catheter while parking the elongate tool device. Notably, during each state, the catheter device is retracting the catheter in a proximal direction. For example, the catheter device is moving in a proximal direction to cause retraction of the catheter in the proximal direction.

In the first state, the proximal elongate tool device is not moving, and the proximal shutter is opening. The distal elongate tool device is not moving and the distal shutter is closed. With the shutter of the distal elongate tool device closed, the distal elongate tool device maintains the position of the elongate tool (e.g., keeps the elongate tool parked). The shutter of the proximal elongate tool device opens to release the elongate tool in preparation for movement of the proximal elongate tool device. This state represents a transition from the fifth configuration to the fourth configuration (see FIG. 12). Notably, the catheter device is moving proximally towards the distal elongate tool device.

In the second state, the proximal elongate tool device is moving proximally, and the proximal shutter is open. The distal elongate tool device is not moving and the distal shutter is closed. With the shutter of the distal elongate tool device closed, the distal elongate tool device maintains the position of the elongate tool (e.g., keeps the elongate tool parked). The shutter of the proximal elongate tool device is open and disengaged to from the elongate tool in preparation for movement of the proximal elongate tool device. The proximal device moves in the proximal direction without affecting the parked position of the elongate tool because of the open shutter. This state represents a transition from the fourth configuration to the third configuration (see FIG. 12). Notably, the catheter device is moving proximally towards the distal elongate tool device.

In the third state, the proximal elongate tool device is not moving, and the proximal shutter is open. The distal elongate tool device is not moving and the distal shutter is closed. With the shutter of the distal elongate tool device closed, the distal elongate tool device maintains the position of the elongate tool (e.g., keeps the elongate tool parked). The shutter of the proximal elongate tool device remains open as the proximal elongate tool device stops moving at its new position. This state represents the third configuration of FIG. 12. Notably, the catheter device is moving proximally towards the distal elongate tool device.

In the fourth state, the proximal elongate tool device is not moving, and the proximal shutter is closing. The distal elongate tool device is not moving and the distal shutter is closed. With the shutter of the distal elongate tool device closed, the distal elongate tool device maintains the position of the elongate tool (e.g., keeps the elongate tool parked). The shutter of the proximal elongate tool device begins closing to engage the elongate tool in preparation for handoff of the elongate tool from the distal elongate tool device to the proximal elongate tool device. This state is representative of a transition from the third configuration to the second configuration (see FIG. 12). Notably, the catheter device is moving proximally towards the distal elongate tool device.

In the fifth state, the proximal elongate tool device is not moving, and the proximal shutter is closed. The distal elongate tool device is not moving and the distal shutter is opening. With the shutter of the proximal elongate tool device now closed, the proximal elongate tool device maintains the position of the elongate tool (e.g., keeps the elongate tool parked). The shutter of the distal elongate tool device is now opening to hand off the elongate tool to the proximal elongate tool device and in preparation for movement of the distal elongate tool device. This state is representative of a transition from the second configuration to the first configuration (see FIG. 12). Notably, the catheter device is moving proximally towards the distal elongate tool device.

In the sixth state, the proximal elongate tool device is not moving, and the proximal shutter is closed. The distal elongate tool device is moving in the proximal direction and the distal shutter is open. With the shutter of the proximal elongate tool device closed, the proximal elongate tool device maintains the position of the elongate tool (e.g., keeps the elongate tool parked). The shutter of the distal elongate tool device is open and disengaged to from the elongate tool in preparation for movement of the distal elongate tool device. The distal elongate tool device moves in the proximal direction without affecting the parked position of the elongate tool because of the open shutter. This state represents a transition from the first configuration to the sixth configuration (see FIG. 12). Notably, the catheter device is moving proximally towards the distal elongate tool device.

In the seventh state, the proximal elongate tool device is not moving, and the proximal shutter is closed. The distal elongate tool device is not moving and the distal shutter is open. With the shutter of the proximal elongate tool device closed, the proximal elongate tool device maintains the position of the elongate tool (e.g., keeps the elongate tool parked). The distal elongate tool device has stopped moving in its new position, notably now farther from the catheter device. This state represents the sixth configuration of FIG. 12.

In the eighth state, the proximal elongate tool device is not moving, and the proximal shutter is closed. The distal elongate tool device is not moving and the distal shutter is closed. With the shutter of the proximal elongate tool device closed, the proximal elongate tool device maintains the position of the elongate tool (e.g., keeps the elongate tool parked). The shutter of the distal elongate tool device is now closing in preparation for a hand off of the elongate tool from the proximal elongate tool device to the distal elongate tool device. This state represents a transition from the sixth configuration to the first configuration (see FIG. 12). Notably, the catheter device is moving proximally towards the distal elongate tool device.

After the eighth state, this cycle can return to the first state. By sequentially moving through these states, the distal elongate tool device and the proximal elongate tool device walk along the parked elongate tool in the proximal direction to maintain a desired position relative to the catheter device as the catheter device moves in the proximal direction.

Figure 13:
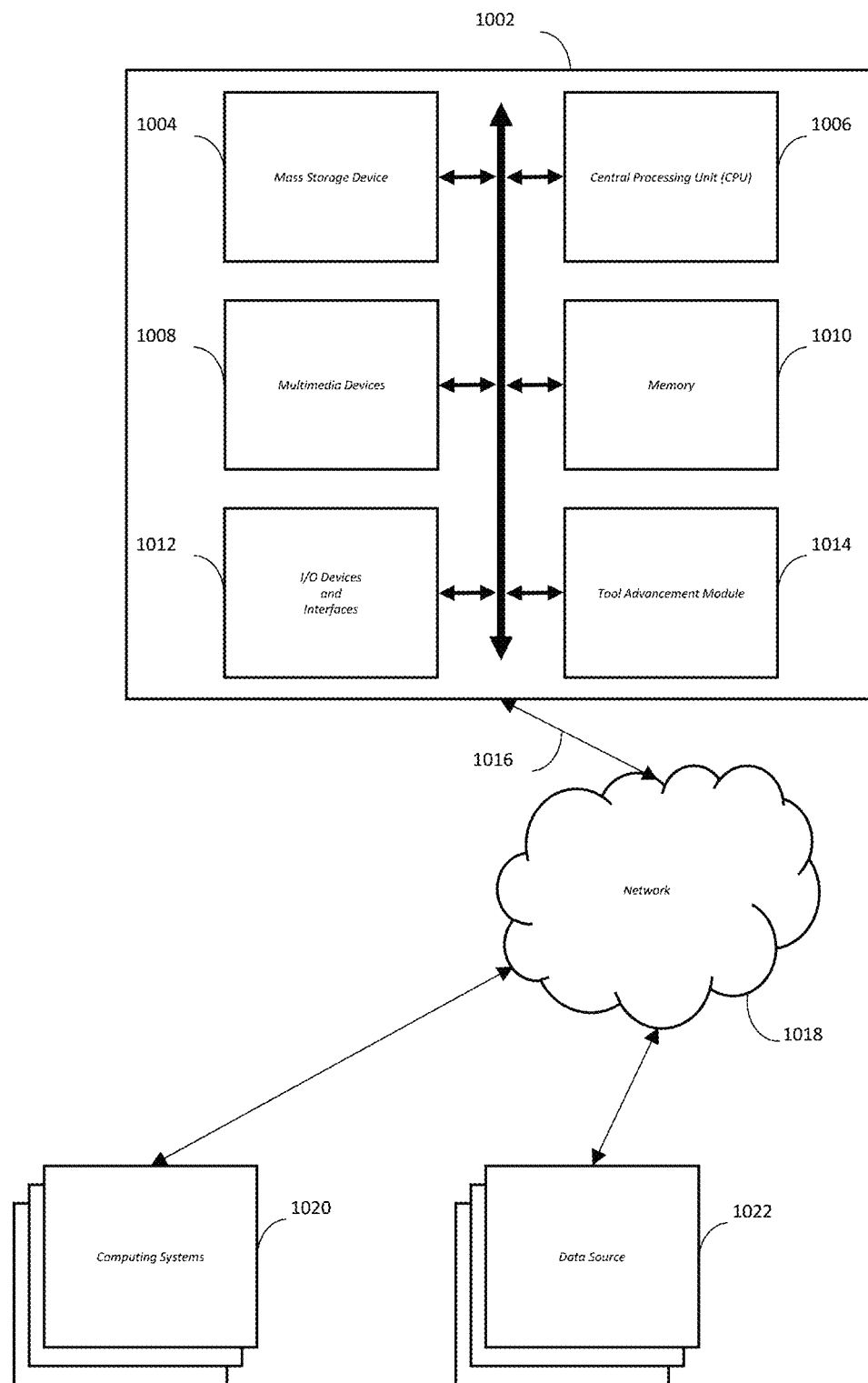
FIG. 13 is a block diagram illustrating an example embodiment of a computer system configured to run software for implementing one or more embodiments of the systems, methods, and devices disclosed herein.

In some embodiments, the systems, processes, and methods described herein are implemented using a computing system, such as the one illustrated in FIG. 13. The example computer system 1002 is in communication with one or more computing systems 1020 and/or one or more data sources 1022 via one or more networks 1018. While FIG. 13 illustrates an embodiment of a computer system 1002, it is recognized that the functionality provided for in the components and modules of computer system 1002 can be combined into fewer components and modules, or further separated into additional components and modules.

The computer system 1002 can comprise a tool advancement module 1014 that carries out the functions, methods, acts, and/or processes described herein. The module 1014 is executed on the computer system 1002 by a central processing unit (CPU) 1006 discussed further below.

In general the word "module," as used herein, refers to logic embodied in hardware or firmware or to a collection of software instructions, having entry and exit points. Modules are written in a program language, such as JAVA, C, C++, and/or the like. Software modules can be compiled or linked into an executable program, installed in a dynamic link library, or can be written in an interpreted language such as BASIC, PERL, LAU, PHP, or Python and/or any such languages. Software modules can be called from other modules or from themselves, and/or can be invoked in response to detected events or interruptions. Modules implemented in hardware include connected logic units such as gates and flip-flops, and/or can include programmable units, such as programmable gate arrays and/or processors.

Generally, the modules described herein refer to logical modules that can be combined with other modules or divided into sub-modules despite their physical organization or storage. The modules are executed by one or more computing systems and can be stored on or within any suitable computer readable medium or implemented inwhole or in-part within special designed hardware or firmware. Not all calculations, analysis, and/or optimization require the use of computer systems, though any of the above-described methods, calculations, processes, or analyses can be facilitated through the use of computers. Further, in some embodiments, process blocks described herein can be altered, rearranged, combined, and/or omitted.

The computer system 1002 includes one or more CPU 1006, which can comprise a microprocessor. The computer system 1002 further includes a physical memory 1010, such as random access memory (RAM) for temporary storage of information, a read only memory (ROM) for permanent storage of information, and a mass storage device 1004, such as a backing store, hard drive, rotating magnetic disks, solid state disks (SSD), flash memory, phase-change memory (PCM), 3D XPoint memory, diskette, or optical media storage device. Alternatively, the mass storage device can be implemented in an array of servers. Typically, the components of the computer system 1002 are connected to the computer using a standards-based bus system. The bus system can be implemented using various protocols, such as Peripheral Component Interconnect (PCI), Micro Channel, SCSI, Industrial Standard Architecture (ISA) and Extended ISA (EISA) architectures.

The computer system 1002 includes one or more input/output (I/O) devices and interfaces 1012, such as a keyboard, mouse, touch pad, and printer. The I/O devices and interfaces 1012 can include one or more display devices, such as a monitor, that allows the visual presentation of data to a user. More particularly, a display device provides for the presentation of GUIs as application software data, and multi-media presentations, for example. The I/O devices and interfaces 1012 can also provide a communications interface to various external devices. The computer system 1002 can comprise one or more multi-media devices 1008, such as speakers, video cards, graphics accelerators, and microphones, for example.

The computer system 1002 can run on a variety of computing devices, such as a server, a Windows server, a Structure Query Language server, a Unix Server, a personal computer, a laptop computer, and so forth. In other embodiments, the computer system 1002 can run on a cluster computer system, a mainframe computer system and/or other computing system suitable for controlling and/or communicating with large databases, performing high volume transaction processing, and generating reports from large databases. The computer system 1002 is generally controlled and coordinated by an operating system software, such as z/OS, Windows, Linux, UNIX, BSD, PHP, SunOS, Solaris, MacOS, ICloud services or other compatible operating systems, including proprietary operating systems. Operating systems control and schedule computer processes for execution, perform memory management, provide file system, networking, and I/O services, and provide a user interface, such as a graphical user interface (GUI), among other things.

The computer system 1002 illustrated in FIG. 13 is coupled to a network 1018, such as a LAN, WAN, or the Internet via a communication link 1016 (wired, wireless, or a combination thereof). Network 1018 communicates with various computing devices and/or other electronic devices. Network 1018 is communicating with one or more computing systems 1020 and one or more data sources 1022. The tool advancement module 1014 can access or can be accessed by computing systems 1020 and/or data sources 1022 through a web-enabled user access point. Connections can be a direct physical connection, a virtual connection, and other connection type. The web-enabled user access point can comprise a browser module that uses text, graphics, audio, video, and other media to present data and to allow interaction with data via the network 1018.

The output module can be implemented as a combination of an all-points addressable display such as a cathode ray tube (CRT), a liquid crystal display (LCD), a plasma display, or other types and/or combinations of displays. The output module can be implemented to communicate with input devices 1012 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module can communicate with a set of input and output devices to receive signals from the user.

The computer system 1002 can include one or more internal and/or external data sources (for example, data sources 1022). In some embodiments, one or more of the data repositories and the data sources described above can be implemented using a relational database, such as DB2, Sybase, Oracle, CodeBase, and Microsoft® SQL Server as well as other types of databases such as a flat-file database, an entity relationship database, and object-oriented database, and/or a record-based database.

The computer system 1002 can also access one or more databases 1022. The databases 1022 can be stored in a database or data repository. The computer system 1002 can access the one or more databases 1022 through a network 1018 or can directly access the database or data repository through I/O devices and interfaces 1012. The data repository storing the one or more databases 1022 can reside within the computer system 1002.

It will now be evident to those skilled in the art that there has been described herein methods, systems, and devices for improved routing of catheters and other devices to targeted anatomical locations using robotically controlled assemblies. Although the inventions hereof have been described by way of several embodiments, it will be evident that other adaptations and modifications can be employed without departing from the spirit and scope thereof. The terms and expressions employed herein have been used as terms of description and not of limitation; and thus, there is no intent of excluding equivalents, but on the contrary it is intended to cover any and all equivalents that may be employed without departing from the spirit and scope of the inventions.

While the disclosure has been described with reference to certain embodiments, it will be understood that various changes may be made, and equivalents may be substituted for elements thereof without departing from the scope of the disclosure. In addition, many modifications will be appreciated to adapt a particular instrument, situation, or material to the teachings of the disclosure without departing from the essential scope thereof. Therefore, it is intended that the disclosure is not limited to the particular embodiment disclosed as the best mode contemplated for carrying out this disclosure, but that the disclosure will include all embodiments falling within the scope of the appended claims.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above but should be determined only by a fair reading of the claims that follow.

While the embodiments disclosed herein are susceptible to various modifications, and alternative forms, specific examples thereof have been shown in the drawings and are herein described in detail. It should be understood, however, that the inventions are not to be limited to the particular forms or methods disclosed, but, to the contrary, the inventions are to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "advancing a catheter or microcatheter" or "advancing one portion of the device (e.g., linearly) relative to another portion of the device to rotate the distal end of the device" include instructing advancing a catheter" or "instructing advancing one portion of the device," respectively. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 mm" includes "10 mm." Terms or phrases preceded by a term such as "substantially" include the recited term or phrase. For example, "substantially parallel" includes "parallel."

What is claimed is:

1. A system for moving an elongate tool through a lumen, the system comprising:
   a proximal device configured to move linearly in proximal and distal directions and comprising a proximal shutter configured to transition between an open state in which an elongate tool moves freely through the proximal shutter and a closed state in which the elongate tool is fixedly held by the proximal shutter;
   a distal device configured to move linearly in the proximal and distal directions and comprising a distal shutter configured to transition between an open state in which the elongate tool moves freely through the distal shutter and a closed state in which the elongate tool is fixedly held by the distal shutter; and
   at least one processor and at least one electronic storage medium, the at least electronic storage medium storing instructions configured to cause the at least one processor to continuously advance the elongate tool in the distal direction by transitioning the distal device and the proximal device through each of the following states sequentially:
      a first state, wherein the proximal device is moving in the distal direction and the proximal shutter is closed, and the distal device is moving in the distal direction and the distal shutter is closing,
      a second state, wherein the proximal device is moving in the distal direction and the proximal shutter is opening, and the distal device is moving in the distal direction and the distal shutter is closed,
      a third state, wherein the proximal device is moving in the proximal direction and the proximal shutter is open, and the distal device is moving in the distal direction and the distal shutter is closed,
      a fourth state, wherein the proximal device is moving in the distal direction and the proximal shutter is open, and the distal device is moving in the distal direction and the distal shutter is closed,
      a fifth state, wherein the proximal device is moving in the distal direction and the proximal shutter is closing, and the distal device is moving in the distal direction and the distal shutter is closed,
      a sixth state, wherein the proximal device is moving in the distal direction and the proximal shutter is closed, and the distal device is moving in the distal direction and the distal shutter is opening,
      a seventh state, wherein the proximal device is moving in the distal direction and the proximal shutter is closed, and the distal device is moving in the proximal direction and the distal shutter is open, and
      an eighth state, wherein the proximal device is moving in the distal direction and the proximal shutter is closed, and the distal device is moving the distal direction and the distal shutter is open.

2. The system of claim 1, wherein, as the distal device and the proximal device sequentially transition through each of the states, the elongate tool advances in a continuous manner.

3. The system of claim 1, wherein, as the distal device and the proximal device sequentially transition through each of the states, the elongate tool advances with a constant velocity.

4. The system of claim 1, wherein the elongate tool comprises a guidewire, a coil, a stent, a flow diverter, or a stent retriever.

5. The system of claim 1, wherein the instructions are configured to cause the at least one processor to begin advancing the elongate tool from any of the states.

6. The system of claim 1, wherein the instructions are configured to cause the at least one processor, using the proximal device and the distal device, to:
   stop inserting the elongate tool in the distal direction; and
   retract the elongate tool in the proximal direction.

7. The system of claim 6, wherein retraction can begin from any of the states.

8. The system of claim 6, wherein retraction is continuous.

9. The system of claim 1, further comprising a catheter device configured to fixedly engage with a catheter, the catheter comprising a lumen with the elongate tool inserted therethrough, the catheter device configured to move linearly in proximal and distal directions, wherein the catheter device is positioned distal to the distal device.

10. The system of claim 9, wherein the instructions are further configured to cause the at least one processor to advance or retract the catheter by moving the catheter device linearly in the distal and proximal directions.

11. The system of claim 9, wherein the elongate tool extends from the lumen of the catheter, through the distal shutter of the distal device, and through the proximal shutter of the proximal device.

12. The system of claim 9, wherein the catheter comprises a microcatheter.

13. A system for moving an elongate tool through a lumen, the system comprising:
   a proximal device configured to move linearly in proximal and distal directions and comprising a proximal shutter configured to transition between an open state in which an elongate tool moves freely through the proximal shutter and a closed state in which the elongate tool is fixedly held by the proximal shutter,
   a distal device configured to move linearly in the proximal and distal directions and comprising a distal shutter configured to transition between an open state in which the elongate tool moves freely through the distal shutter and a closed state in which the elongate tool is fixedly held by the distal shutter; and
   at least one processor and at least one electronic storage medium, the at least electronic storage medium storing instructions configured to cause the at least one processor to continuously retract the elongate tool in the proximal direction by transitioning the distal device and the proximal device through each of the following states sequentially:
      a first state, wherein the proximal device is moving in the proximal direction and the proximal shutter is closing, and the distal device is moving in the proximal direction and the distal shutter is closed;
      a second state, wherein the proximal device is moving in the proximal direction and the proximal shutter is closed, and the distal device is moving in the proximal direction and the distal shutter is opening,
      a third state, wherein the proximal device is moving in the proximal direction and the proximal shutter is closed, and the distal device is moving in the distal direction and the distal shutter is open, a fourth state, wherein the proximal device is moving in the proximal direction and the proximal shutter is closed, and the distal device is moving in the proximal direction and the distal shutter is open, a fifth state, wherein the proximal device is moving in the proximal direction and the proximal shutter is closed, and the distal device is moving in the proximal direction and the distal shutter is closing, a sixth state, wherein the proximal device is moving in the proximal direction and the proximal shutter is opening, and the distal device is moving in the proximal direction and the distal shutter is closed, a seventh state, wherein the proximal device is moving in the distal direction and the proximal shutter is open, and the distal device is moving in the proximal direction and the distal shutter is closed, and an eighth state, wherein the proximal device is moving in the proximal direction and the proximal shutter is closing, and the distal device is moving in the proximal direction and the distal shutter is closed.

14. The system of claim 13, wherein, as the distal device and the proximal device sequentially transition through each of the states, the elongate tool retracts in a continuous manner.

15. The system of claim 13, wherein, as the distal device and the proximal device sequentially transition through each of the states, the elongate tool retracts with a constant velocity.

16. The system of claim 13, wherein the elongate tool comprises a guidewire, a coil, a stent, a flow diverter, or a stent retriever.

17. The system of claim 13, wherein the instructions are configured to cause the at least one processor to begin retracting the elongate tool from any of the states.

18. The system of claim 13, wherein the instructions are configured to cause the at least one processor, using the proximal device and the distal device, to:

stop retracting the elongate tool in the proximal direction; and insert the elongate tool in the distal direction.

19. The system of claim 18, wherein insertion can begin from any of the states.

20. The system of claim 18, wherein insertion is continuous.

21. The system of claim 13, further comprising a catheter device configured to fixedly engage with a catheter, the catheter comprising a lumen with the elongate tool inserted therethrough, the catheter device configured to move linearly in proximal and distal directions, wherein the catheter device is positioned distal to the distal device.

22. The system of claim 21, wherein the instructions are further configured to cause the at least one processor to advance or retract the catheter by moving the catheter device linearly in the distal and proximal directions.

23. The system of claim 21, wherein the elongate tool extends from the lumen of the catheter, through the distal shutter of the distal device, and through the proximal shutter of the proximal device.

24. The system of claim 21, wherein the catheter comprises a microcatheter.

* * * * *